United States Patent
Tibbles et al.

(10) Patent No.: US 11,834,473 B2
(45) Date of Patent: Dec. 5, 2023

(54) ENGINEERED O-GLYCOSYLATION IN RECOMBINANT POLYPEPTIDES AND USES THEREOF

(71) Applicant: MedImmune Limited, Cambridge (GB)

(72) Inventors: Adam Tibbles, Cambridge (GB); Monika Papworth, Cambridge (GB); Daniel Higazi, Cambridge (GB); Emmanuel Rossy, Cambridge (GB); Katarzyna Anna Kozakowska, Cambridge (GB); Thomas Vincent Murray, Cambridge (GB)

(73) Assignee: MedImmune Limited, Cambridge (GB)

( * ) Notice: Subject to any disclaimer, the term of this patent is extended or adjusted under 35 U.S.C. 154(b) by 248 days.

(21) Appl. No.: 16/956,006

(22) PCT Filed: Dec. 20, 2018

(86) PCT No.: PCT/EP2018/086385
§ 371 (c)(1),
(2) Date: Jun. 19, 2020

(87) PCT Pub. No.: WO2019/122234
PCT Pub. Date: Jun. 27, 2019

(65) Prior Publication Data
US 2020/0317724 A1 Oct. 8, 2020

Related U.S. Application Data

(60) Provisional application No. 62/608,812, filed on Dec. 21, 2017.

(51) Int. Cl.
| | |
|---|---|
| *A61K 47/62* | (2017.01) |
| *C07K 1/107* | (2006.01) |
| *C07K 9/00* | (2006.01) |
| *C07K 14/605* | (2006.01) |
| *C12P 21/00* | (2006.01) |
| *A61K 38/00* | (2006.01) |

(52) U.S. Cl.
CPC .......... *C07K 1/1077* (2013.01); *A61K 47/62* (2017.08); *C07K 9/001* (2013.01); *C07K 14/605* (2013.01); *C12P 21/005* (2013.01); *A61K 38/00* (2013.01); *C07K 2319/30* (2013.01)

(58) Field of Classification Search
CPC ........ C12P 21/00; C07K 14/605; A61K 38/00
See application file for complete search history.

(56) References Cited

U.S. PATENT DOCUMENTS

| 9,187,532 B2 * | 11/2015 | DeFrees ............... A61K 47/644 |
| 2008/0255040 A1 | 10/2008 | DeFrees |

FOREIGN PATENT DOCUMENTS

| WO | 2015/022420 A1 | 2/2015 |
| WO | 2016/118577 A1 | 7/2016 |

OTHER PUBLICATIONS

Vocadlo D et al, "A chemical approach for identifying O-GlcNAc-modified proteins in cells", Proceedings of the National Academy of Sciences of the USA, 2003, vol. 100, No. 16, pp. 9116-9121.
Chao Pan et al, "Biosynthesis of Conjugate Vaccines Using an O-Linked Glycosylation System", MBIO, 2016, vol. 7, No. 2, e00443-16, pp. 1-11.
P. Hossler et al, "Optimal and consistent protein glycosylation in mammalian cell culture", Glycobiology, 2009, vol. 19, No. 9, pp. 936-949.
Xiu Zhang et al., "Applications of Azide-Based Bioorthogonal Click Chemistry in Glycobiology", Molecules, 2013, vol. 18, No. 6, pp. 7145-7159.
Zhu Y. et al., Coccidioides immitis Antigen 2: analysis of gene and protein, Gene, 1996, vol. 181, pp. 121-125.

\* cited by examiner

*Primary Examiner* — Tekchand Saidha

(57) ABSTRACT

The present invention relates to recombinant polypeptide therapeutics having an engineered O-linked amino acid (AA) glycosylation sequence (motif), which is covalently linked to O-glycan(s) (tag). Recombinant O-glycosylated polypeptides may be produced in mammalian cells to present natural or un-natural O-glycan structures through metabolic labelling.

4 Claims, 12 Drawing Sheets

Specification includes a Sequence Listing.

```
                          SEQUENCE LISTING

<160> NUMBER OF SEQ ID NOS: 43

<210> SEQ ID NO 1
<211> LENGTH: 27
<212> TYPE: PRT
<213> ORGANISM: Artificial Sequence
<220> FEATURE:
<223> OTHER INFORMATION: i0

<400> SEQUENCE: 1

Glu Phe Ile Ala Trp Leu Val Lys Gly Ala Ala Ala Gly Gly Ser Gly
1               5                   10                  15

Ser Thr Ala Ser Ser Gly Ser Gly Ser Ala Thr
            20                  25

<210> SEQ ID NO 2
<211> LENGTH: 19
<212> TYPE: PRT
<213> ORGANISM: Artificial Sequence
<220> FEATURE:
<223> OTHER INFORMATION: i1

<400> SEQUENCE: 2

Lys Asn Pro Leu Pro Thr Lys Glu Thr Ile Glu Gln Glu Lys Gln Ala
1               5                   10                  15

Gly Glu Ser

<210> SEQ ID NO 3
<211> LENGTH: 19
<212> TYPE: PRT
<213> ORGANISM: Artificial Sequence
<220> FEATURE:
<223> OTHER INFORMATION: i1+10T

<400> SEQUENCE: 3

Lys Asn Pro Leu Pro Thr Lys Glu Thr Ile Glu Gln Glu Lys Gln Thr
1               5                   10                  15

Gly Glu Ser

<210> SEQ ID NO 4
<211> LENGTH: 14
<212> TYPE: PRT
<213> ORGANISM: Artificial Sequence
<220> FEATURE:
<223> OTHER INFORMATION: i2

<400> SEQUENCE: 4

Lys Asn Pro Leu Pro Thr Lys Glu Thr Ile Glu Gln Glu Lys
1               5                   10

<210> SEQ ID NO 5
<211> LENGTH: 20
<212> TYPE: PRT
<213> ORGANISM: Artificial Sequence
<220> FEATURE:
<223> OTHER INFORMATION: i1-11T
<220> FEATURE:
<221> NAME/KEY: MISC_FEATURE
<222> LOCATION: (2)..(6)
```

<223> OTHER INFORMATION: X is any amino acid

<400> SEQUENCE: 5

Thr Xaa Xaa Xaa Xaa Xaa Lys Asn Pro Leu Pro Thr Lys Glu Ala Ile
1               5                   10                  15

Glu Gln Glu Lys
            20

<210> SEQ ID NO 6
<211> LENGTH: 11
<212> TYPE: PRT
<213> ORGANISM: Artificial Sequence
<220> FEATURE:
<223> OTHER INFORMATION: i3

<400> SEQUENCE: 6

Lys Asn Pro Leu Pro Thr Lys Glu Thr Ile Glu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: i4

<400> SEQUENCE: 7

Lys Asn Pro Leu Pro Thr Lys Glu Thr
1               5

<210> SEQ ID NO 8
<211> LENGTH: 6
<212> TYPE: PRT
<213> ORGANISM: Artificial Sequence
<220> FEATURE:
<223> OTHER INFORMATION: i6

<400> SEQUENCE: 8

Pro Leu Pro Thr Lys Glu
1               5

<210> SEQ ID NO 9
<211> LENGTH: 6
<212> TYPE: PRT
<213> ORGANISM: Artificial Sequence
<220> FEATURE:
<223> OTHER INFORMATION: i6 +1A

<400> SEQUENCE: 9

Pro Leu Pro Thr Ala Glu
1               5

<210> SEQ ID NO 10
<211> LENGTH: 7
<212> TYPE: PRT
<213> ORGANISM: Artificial Sequence
<220> FEATURE:
<223> OTHER INFORMATION: i6 +3P

<400> SEQUENCE: 10

Pro Leu Pro Thr Lys Glu Pro
1               5

<210> SEQ ID NO 11
<211> LENGTH: 7
<212> TYPE: PRT

```
<213> ORGANISM: Artificial Sequence
<220> FEATURE:
<223> OTHER INFORMATION: i6 dbl

<400> SEQUENCE: 11

Pro Leu Pro Thr Ala Glu Pro
1               5

<210> SEQ ID NO 12
<211> LENGTH: 5
<212> TYPE: PRT
<213> ORGANISM: Artificial Sequence
<220> FEATURE:
<223> OTHER INFORMATION: i7 dbl

<400> SEQUENCE: 12

Pro Thr Ala Glu Pro
1               5

<210> SEQ ID NO 13
<211> LENGTH: 5
<212> TYPE: PRT
<213> ORGANISM: Artificial Sequence
<220> FEATURE:
<223> OTHER INFORMATION: i8 P-1A

<400> SEQUENCE: 13

Ala Thr Ala Glu Pro
1               5

<210> SEQ ID NO 14
<211> LENGTH: 5
<212> TYPE: PRT
<213> ORGANISM: Artificial Sequence
<220> FEATURE:
<223> OTHER INFORMATION: O-linked glycosylation sequence

<400> SEQUENCE: 14

Pro Thr Ala Glu Ala
1               5

<210> SEQ ID NO 15
<211> LENGTH: 9
<212> TYPE: PRT
<213> ORGANISM: Artificial Sequence
<220> FEATURE:
<223> OTHER INFORMATION: O-linked glycosylation sequence

<400> SEQUENCE: 15

Ala Ala Pro Gly Pro Thr Pro Gly Pro
1               5

<210> SEQ ID NO 16
<211> LENGTH: 9
<212> TYPE: PRT
<213> ORGANISM: Artificial Sequence
<220> FEATURE:
<223> OTHER INFORMATION: O-linked glycosylation sequence

<400> SEQUENCE: 16

Ala Ala Val Gly Ala Thr Val Glu Gly
1               5

<210> SEQ ID NO 17
<211> LENGTH: 9
<212> TYPE: PRT
<213> ORGANISM: Artificial Sequence
```

```
<220> FEATURE:
<223> OTHER INFORMATION: O-linked glycosylation sequence

<400> SEQUENCE: 17

Ala Ala Asp Ser Thr Thr Pro Ala Pro
1               5

<210> SEQ ID NO 18
<211> LENGTH: 9
<212> TYPE: PRT
<213> ORGANISM: Artificial Sequence
<220> FEATURE:
<223> OTHER INFORMATION: O-linked glycosylation sequence

<400> SEQUENCE: 18

Ala Ala Ser Leu Pro Ser Ile Ser Ser
1               5

<210> SEQ ID NO 19
<211> LENGTH: 20
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 19

Lys Gly Ala Ala Ala Gly Gly Ser Gly Ser Thr Ala Ser Ser Gly Ser
1               5                   10                  15

Gly Ser Ala Thr
            20

<210> SEQ ID NO 20
<211> LENGTH: 33
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 20

Lys Gly Lys Asn Pro Leu Pro Thr Lys Glu Thr Ile Glu Gln Glu Lys
1               5                   10                  15

Gln Ala Gly Glu Ser Ala Ala Ala Gly Ser Ser Gly Ser Gly Ser Ala
            20                  25                  30

Thr

<210> SEQ ID NO 21
<211> LENGTH: 33
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 21

Lys Gly Lys Asn Pro Leu Pro Thr Lys Glu Thr Ile Glu Gln Glu Lys
1               5                   10                  15

Gln Thr Gly Glu Ser Ala Ala Ala Gly Ser Ser Gly Ser Gly Ser Ala
            20                  25                  30

Thr

<210> SEQ ID NO 22
<211> LENGTH: 28
<212> TYPE: PRT
<213> ORGANISM: Artificial Sequence
<220> FEATURE:
```

-continued

```
<223> OTHER INFORMATION: O-glycosylation of GLP-1:Fc fusion protein

<400> SEQUENCE: 22

Lys Gly Lys Asn Pro Leu Pro Thr Lys Glu Thr Ile Glu Gln Glu Lys
1               5                   10                  15

Gly Ser Thr Ala Ser Ser Gly Ser Gly Ser Ala Thr
            20                  25

<210> SEQ ID NO 23
<211> LENGTH: 28
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 23

Lys Gly Lys Asn Pro Leu Pro Thr Lys Glu Thr Ile Glu Gln Glu Lys
1               5                   10                  15

Gly Ser Thr Ala Ser Ser Gly Ser Gly Ser Ala Thr
            20                  25

<210> SEQ ID NO 24
<211> LENGTH: 28
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 24

Lys Gly Lys Asn Pro Leu Pro Thr Lys Glu Ala Ile Glu Gln Glu Lys
1               5                   10                  15

Gly Ser Thr Ala Ser Ser Gly Ser Gly Ser Ala Thr
            20                  25

<210> SEQ ID NO 25
<211> LENGTH: 28
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 25

Lys Gly Lys Asn Pro Leu Pro Thr Lys Glu Thr Ile Glu Gln Glu Lys
1               5                   10                  15

Gly Ala Ala Ala Ser Ser Gly Ser Gly Ser Ala Thr
            20                  25

<210> SEQ ID NO 26
<211> LENGTH: 25
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 26

Lys Gly Lys Asn Pro Leu Pro Thr Lys Glu Thr Ile Glu Gly Ser Thr
1               5                   10                  15

Ala Ser Ser Gly Ser Gly Ser Ala Thr
            20                  25

<210> SEQ ID NO 27
<211> LENGTH: 25
<212> TYPE: PRT
<213> ORGANISM: Artificial Sequence
```

```
<220> FEATURE:
<223> OTHER INFORMATION: O-glycosylation of GLP-1:Fc fusion protein

<400> SEQUENCE: 27

Lys Gly Lys Asn Pro Leu Pro Thr Lys Glu Thr Gly Ser Thr Ala Ser
1               5                   10                  15

Ser Gly Ser Gly Ser Gly Ser Ala Thr
            20                  25

<210> SEQ ID NO 28
<211> LENGTH: 22
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 28

Lys Gly Lys Asn Pro Leu Pro Thr Lys Glu Gly Ser Thr Ala Ser Ser
1               5                   10                  15

Gly Ser Gly Ser Ala Thr
            20

<210> SEQ ID NO 29
<211> LENGTH: 12
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 29

Lys Gly Pro Leu Pro Thr Lys Glu Gly Ser Ala Thr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 30

Lys Gly Pro Leu Pro Thr Ala Glu Gly Ser Ala Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 31

Lys Gly Pro Leu Pro Thr Lys Glu Pro Gly Ser Ala Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 32

Lys Gly Pro Leu Pro Thr Ala Glu Pro Gly Ser Ala Thr
1               5                   10
```

<210> SEQ ID NO 33
<211> LENGTH: 11
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 33

Lys Gly Pro Thr Lys Glu Arg Gly Ser Ala Thr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 34

Lys Gly Pro Thr Ala Glu Pro Gly Ser Ala Thr
1               5                   10

<210> SEQ ID NO 35
<211> LENGTH: 15
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 35

Lys Gly Ala Thr Ala Glu Pro Gly Ser Thr Ala Ser Ser Gly Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 36

Lys Gly Pro Thr Ala Glu Ala Gly Ser Thr Ala Ser Ser Gly Ser
1               5                   10                  15

<210> SEQ ID NO 37
<211> LENGTH: 23
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 37

Lys Gly Ala Ala Pro Gly Pro Thr Pro Gly Pro Gly Ser Thr Ala Ser
1               5                   10                  15

Ser Gly Ser Gly Ser Ala Thr
            20

<210> SEQ ID NO 38
<211> LENGTH: 23
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 38

Lys Gly Ala Ala Val Gly Ala Thr Val Glu Gly Gly Ser Thr Ala Ser

```
-continued 1               5                   10                  15
Ser Gly Ser Gly Ser Ala Thr
            20

<210> SEQ ID NO 39
<211> LENGTH: 23
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 39

Lys Gly Ala Ala Asp Ser Thr Thr Pro Ala Pro Gly Ser Thr Ala Ser
1               5                   10                  15

Ser Gly Ser Gly Ser Ala Thr
            20

<210> SEQ ID NO 40
<211> LENGTH: 23
<212> TYPE: PRT
<213> ORGANISM: Artificial Sequence
<220> FEATURE:
<223> OTHER INFORMATION: O-glycosylation of GLP-1:Fc fusion protein

<400> SEQUENCE: 40

Lys Gly Ala Ala Ser Leu Pro Ser Ile Ser Ser Gly Ser Thr Ala Ser
1               5                   10                  15

Ser Gly Ser Gly Ser Ala Thr
            20

<210> SEQ ID NO 41
<211> LENGTH: 6
<212> TYPE: PRT
<213> ORGANISM: Artificial Sequence
<220> FEATURE:
<223> OTHER INFORMATION: O-glycosylation sequence

<400> SEQUENCE: 41

Pro Thr Ala Glu Pro Gly
1               5

<210> SEQ ID NO 42
<211> LENGTH: 11
<212> TYPE: PRT
<213> ORGANISM: Artificial Sequence
<220> FEATURE:
<223> OTHER INFORMATION: O-glycosylation sequence
<220> FEATURE:
<221> NAME/KEY: MISC_FEATURE
<222> LOCATION: (1)..(3)
<223> OTHER INFORMATION: X is any amino acid
<220> FEATURE:
<221> NAME/KEY: MISC_FEATURE
<222> LOCATION: (9)..(11)
<223> OTHER INFORMATION: X is any amino acid

<400> SEQUENCE: 42

Xaa Xaa Xaa Pro Ala Ala Glu Lys Xaa Xaa Xaa
1               5                   10

<210> SEQ ID NO 43
<211> LENGTH: 11
<212> TYPE: PRT
<213> ORGANISM: Artificial Sequence
<220> FEATURE:
<223> OTHER INFORMATION: O-glycosylation sequence
<220> FEATURE:
```

```
<221> NAME/KEY: MISC_FEATURE
<222> LOCATION: (1)..(3)
<223> OTHER INFORMATION: X is any amino acid
<220> FEATURE:
<221> NAME/KEY: MISC_FEATURE
<222> LOCATION: (9)..(11)
<223> OTHER INFORMATION: X is any amino acid

<400> SEQUENCE: 43

Xaa Xaa Xaa Pro Thr Ala Glu Pro Xaa Xaa Xaa
1               5                   10
```

ENGINEERED O-GLYCOSYLATION IN RECOMBINANT POLYPEPTIDES AND USES THEREOF

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 11,891 Byte ASCII (Text) file named "OGLYC-100-US-PSP-SequenceListing.TXT," created on Dec. 21, 2017.

FIELD OF THE INVENTION

The present invention relates to recombinant polypeptide therapeutics having an engineered O-linked amino acid (AA) glycosylation sequence (motif), which is covalently linked to O-glycan(s) (tag). Recombinant O-glycosylated polypeptides may be produced in mammalian cells to present natural or un-natural O-glycan structures through metabolic labelling. Polypeptides produced by this method may benefit from engineered O-glycan structures which provide additional functionality; most notably the possibility of adding functional moieties by chemical conjugation to the engineered O-glycans.

BACKGROUND

Protein glycosylation is a common and highly diverse post translational modification (PTM). In eukaryotic cells such modifications can be divided into two broad categories, N-linked glycosylation and O-linked glycosylation. Typically extracellularly; in N-linked glycosylation, the oligosaccharide is covalently attached to an asparagine, whereas in O-linked glycosylation, the attachment usually occurs on the hydroxyl group of either serine or tyrosine.

There is great diversity in the structures created by glycosylation reactions, for O-linked mucin-type glycans, found on secreted and cell surface associated glycoproteins, this variation is produced by the activity of specific transferase enzymes that are resident in the secretory pathway (notably the Golgi apparatus). They catalyse the maturation of O-glycans through sequential monosaccharide condensations to/beyond the precursor N-acetylgalactosamine (O-GalNAc, Tn antigen), itself placed by the action of polypeptide N-acetlygalactosaminyltransferase (ppGalNAc-T) isoenzymes. Diversity exists at the level of the glycan structure per se and in the positions of attachment of the O-glycans to the protein backbones, something exquisitely controlled by the unique interplay of O-glycosylation sequence motif and oligosaccharide transferase expression alongside nutrient availability and cellular activity. Specifics of this process are currently only vaguely understood.

In nature O-glycans impart a number of desirable effects afforded by such properties as hydration/charge, protein-protein interaction, backbone exposure/accessibility and surface epitope/recognition. For example, the presence of O-glycans in a polypeptide may impart characteristics such as barriers/lubrication (en masse), increased half-life (protease/degradation resistance), activity attenuation (protein trafficking, receptor signalling) and protein folding/aggregation state. Non-natural O-glycans may provide further desirable properties. For example, the presence of an O-glycan in a polypeptide may impart improved pharmaceutical behaviour, such as formulation, half-life extension or altered immunogenicity. In a further advancement, the engineering of non-natural O-glycan composition (or location) in a polypeptide may also be exploited. For example, being receptive to subsequent chemical reactions, such as Click chemistry conjugations. These many properties may be exploited in the engineered therapeutic polypeptide.

O-linked glycosylation can be introduced into a polypeptide to exploit one or more of the properties of O-glycans. However, not all polypeptides have an O-linked glycosylation sequence as part of their amino acid sequence. In addition, O-glycosylation of existing O-linked glycosylation sequences may not proceed efficiently and/or O-glycans present through glycosylation of existing O-linked glycosylation sequences may not be optimal for exploitation. Thus, a need exists for engineering O-glycosylation sites into polypeptides.

U.S. Pat. No. 9,187,532 is concerned with the incorporation of exogenous glycosylation sites into proteins such as BMP-7, NT-3 and FGF-21. According to the methodology of U.S. Pat. No. 9,187,532, mutant proteins having an exogenous O-linked glycosylation sequence were expressed in *E. coli* cells and purified. Glycosylation was then subsequently attempted by in vitro addition of GalNAc to the purified proteins.

Although methods for the introduction of O-glycans into proteins exist, as described above and in others (see Invitrogen Click-IT technology), they do not satisfactorily address the need for (i) control over the location of O-glycosylation motifs such that they are specifically and reproducibly O-glycosylated, (ii) high efficiency production of polypeptides with O-glycan tags with commercially viable yields and (iii) potential to modify O-glycan tags to provide additional functionality. The present invention provides solutions to these issues by providing expression 'systems' which uniquely address the need for a reliable and effective means of integrating O-glycan tags into recombinant polypeptides.

SUMMARY OF THE DISCLOSURE

The present invention is concerned with a method for producing an O-glycosylated recombinant therapeutic polypeptide and conjugates thereof. In connection therewith, the invention provides an O-glycosylated recombinant therapeutic polypeptide, an O-glycosylated recombinant therapeutic polypeptide conjugate, pharmaceutical compositions comprising the same, and uses of the same including methods of treatment. The present invention is also concerned with the use of cell culture medium comprising reagents for O-glycosylation for producing an O-glycosylated recombinant therapeutic polypeptide from a host therapeutic polypeptide and cell-line modifications which may further facilitate this process.

Aspects and embodiments of the invention are set out in the appended claims. These and other aspects and embodiments of the invention are also described herein.

BRIEF DESCRIPTION OF FIGURES

Embodiments of the disclosure will now be described, by way of example only, with reference to the accompanying drawings, in which.

Figure Legends

DETAILED DESCRIPTION OF THE INVENTION

Figure 1:
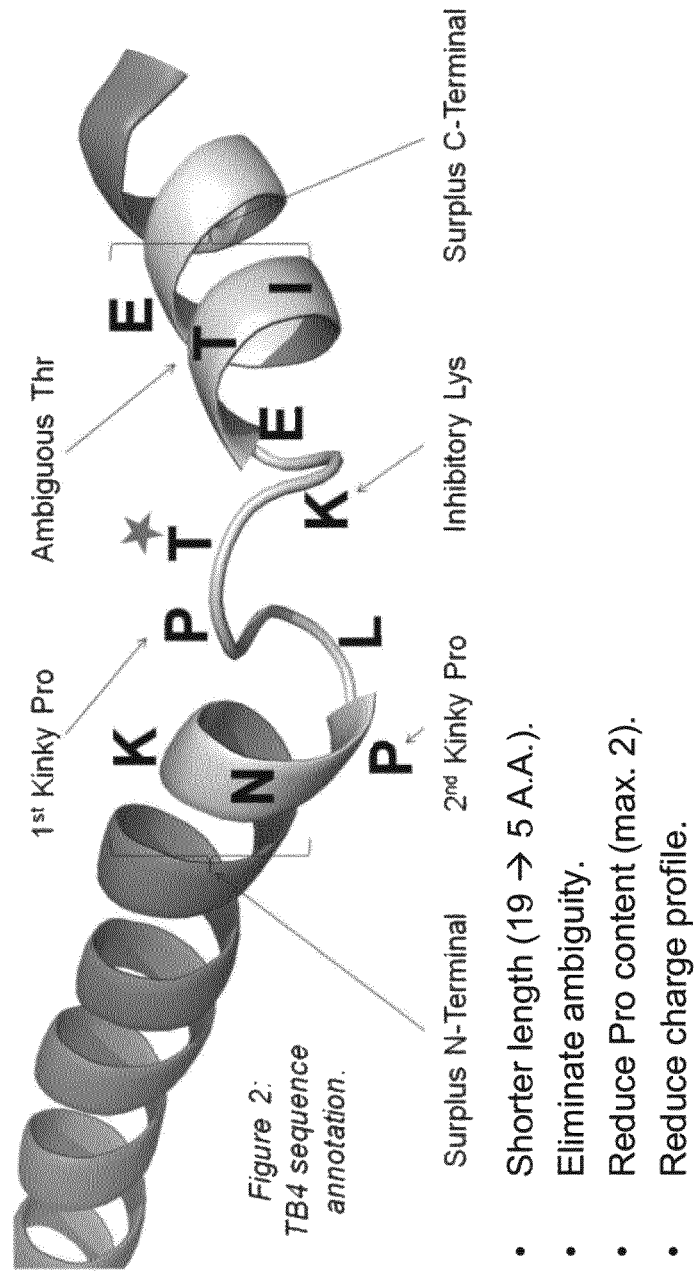
FIG. 1 shows an annotated ribbon structure and amino acid sequence of the TB4 peptide at the site of O-glycosylation.

The present invention provides a method for producing an O-glycosylated recombinant therapeutic polypeptide, the method comprising:
 a. expressing an engineered therapeutic polypeptide in a host cell in the presence of cell culture medium, wherein
   i. the engineered therapeutic polypeptide comprises at least one O-linked glycosylation sequence, and
   ii. the cell culture medium comprises reagents for O-glycosylation,
  such that the at least one engineered O-linked glycosylation sequence is covalently bound to an O-glycan in the recombinant therapeutic polypeptide; and
 b. optionally purifying the recombinant therapeutic polypeptide.

By adding specific reagents for O-glycosylation to the cell culture medium, the inventors discovered that the expressed engineered therapeutic polypeptide can be efficiently and consistently glycosylated with O-glycan at the site of the engineered O-linked glycosylation sequence. The increased efficiency of the O-glycosylation provides for the first time the possibility of producing O-glycosylated recombinant therapeutic polypeptide at yields viable for commercial production. The present invention thus provides an improved method for producing an O-glycosylated recombinant therapeutic polypeptide.

In one embodiment, the method of the invention further comprises
 a. obtaining an expression vector comprising DNA encoding the engineered therapeutic polypeptide comprising the at least one engineered O-linked glycosylation sequence; and
 b. transfecting a host cell with the expression vector.

The present invention provides use of cell culture medium comprising reagents for O-glycosylation for producing an O-glycosylated recombinant therapeutic polypeptide from a host cell expressing an engineered therapeutic polypeptide, wherein
 a. the engineered therapeutic polypeptide comprises at least one engineered O-linked glycosylation sequence; and
 b. the recombinant therapeutic polypeptide comprises the at least one engineered O-linked glycosylation sequence covalently bound to at least one O-glycan.

The O-linked glycosylation sequence may be endogenous to the therapeutic polypeptide. The engineered O-linked glycosylation sequence may be exogenous to the therapeutic polypeptide. Both natural and non-natural O-linked glycosylation sequences may be engineered into the therapeutic polypeptide by methods well known to the person skilled in the art.

The engineered O-linked glycosylation sequence is thus present in both (i) the engineered therapeutic polypeptide expressed in a host cell and (ii) the O-glycosylated recombinant therapeutic polypeptide of the invention produced by the methods of the invention described herein.

The present invention further provides an O-glycosylated recombinant therapeutic polypeptide produced according to the methods as defined above. The present invention further provides an O-glycosylated recombinant therapeutic polypeptide capable of being produced according to the methods as defined above. An O-glycosylated recombinant therapeutic polypeptide having the features of an O-glycosylated recombinant therapeutic polypeptide produced according to the methods as defined above is also within the scope of the present invention.

The O-glycosylated recombinant therapeutic polypeptide of the invention will be understood to be modified as compared with a naturally-occurring glycosylated protein because of the O-linked glycosylation sequence which has been engineered into the protein and the presence of an O-glycan covalently bound to the engineered O-linked glycosylation sequence. The O-glycosylated recombinant therapeutic polypeptide of the invention will be understood to be modified as compared with an engineered therapeutic polypeptide which might comprise a glycosylation sequence because of the metabolic addition of an O-glycan covalently bound to the O-linked glycosylation sequence.

Further, it will be understood that the O-glycosylated recombinant therapeutic polypeptide produced by the method of the invention is identifiable by the fact that, apart from the engineered O-linked glycosylation sequence, the protein will otherwise have glycosylation patterns resulting from glycosylation of the expressed engineered therapeutic polypeptide in cells. Specific culture conditions—cell-type, glucose availability, stresses, enzyme KO—will affect the type of glycan present.

Thus, the present invention provides an O-glycosylated recombinant therapeutic polypeptide comprising at least one O-linked glycosylation sequence covalently bound to at least one O-glycan, wherein the recombinant therapeutic polypeptide comprises natural or un-natural glycosylation patterns/constitution.

The engineered O-linked glycosylation sequences described herein may impart advantageous properties to the O-glycosylated recombinant therapeutic polypeptide of the invention. For example the structure and function (flexibility, accessibility, bioactivity), physicochemical and biophysical properties (pI, solubility, hydrodynamic radius), modulation of protein-protein interactions (including reduced self-association, aggregation and protease resistance), immunogenicity (masking epitopes), product differentiation, and bioprocessing. In a particular example presence of the engineered O-linked glycosylation sequence may reduce proteolysis of the O-glycosylated recombinant therapeutic polypeptide of the invention. In turn, the presence of an engineered O-linked glycosylation sequence may increase the half-life of the O-glycosylated recombinant therapeutic polypeptide of the invention as compared to the therapeutic polypeptide without the engineered O-linked glycosylation sequence. The engineered O-linked glycosylation sequences described herein provide the ability to precisely target O-glycan modification of the O-glycosylated recombinant therapeutic polypeptide of the invention.

In still another aspect, a further molecule can be attached to the O-glycan to form an O-glycosylated recombinant therapeutic polypeptide conjugate. The present invention thus provides an O-glycosylated recombinant therapeutic polypeptide conjugate comprising an O-glycosylated recombinant therapeutic polypeptide as defined anywhere above, wherein a further molecule M is covalently linked to the O-glycan.

In still another aspect, a further molecule can be attached to the O-glycan to form an O-glycosylated recombinant therapeutic polypeptide conjugate comprising the formula:

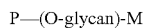

where P represents the engineered recombinant therapeutic polypeptide and M represents a molecule desirable to be attached to P. The O-glycan thus acts as a linking group between P and M.

In still another aspect, the present invention provides a method for producing an O-glycosylated recombinant therapeutic polypeptide conjugate comprising the formula:

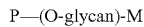

where P represents the engineered recombinant therapeutic polypeptide of the invention and M represents a molecule desirable to be attached to P. The method comprises:
  (i) providing an O-glycosylated recombinant therapeutic polypeptide of the invention; and
  (ii) reacting the O-glycan with M so as to link M to the O-glycan.

It will be understood that the O-glycan must have a reactive group capable of reacting with the reactive group of M so as to link M and the O-glycan. In an embodiment the link may be a covalent link.

In one embodiment, the reacting comprises an azide-alkyne coupling reaction.

The present invention provides an O-glycosylated recombinant therapeutic polypeptide conjugate produced according to the methods as defined above. The present invention further provides an O-glycosylated recombinant therapeutic polypeptide conjugate capable of being produced according to the methods as defined above. An O-glycosylated recombinant therapeutic polypeptide conjugate having the features of an O-glycosylated recombinant therapeutic polypeptide conjugate produced according to the methods as defined above, is also within the scope of the present invention.

The present invention provides a pharmaceutical composition comprising the O-glycosylated recombinant therapeutic polypeptide of the invention and a pharmaceutically acceptable excipient.

The present invention also provides a pharmaceutical composition comprising the O-glycosylated recombinant therapeutic polypeptide conjugate of the invention and a pharmaceutically acceptable excipient.

The present invention provides a method of treating or preventing disease in a patient, the method comprising administering to the patient an O-glycosylated recombinant therapeutic polypeptide of the invention. The present invention also provides a method of treating or preventing disease in a patient, the method comprising administering to the patient an O-glycosylated recombinant therapeutic polypeptide conjugate of the invention. The present invention also provides a method of treating or preventing disease in a patient, the method comprising administering to the patient a receptive O-glycosylated recombinant therapeutic polypeptide and co-administered substrate M to produce the conjugate of the invention.

The present invention provides an O-glycosylated recombinant therapeutic polypeptide of the invention for use as a medicament. The present invention also provides an O-glycosylated recombinant therapeutic polypeptide conjugate of the invention for use as a medicament.

In another aspect, the present invention provides second medical uses of the above mentioned products.

The O-Glycosylated Recombinant Therapeutic Polypeptide

In one embodiment, the O-glycosylated recombinant therapeutic polypeptide of the invention has a molecular weight below 30 kDa. In one embodiment, the O-glycosylated recombinant therapeutic polypeptide of the invention has a molecular weight of around 30 kDa or higher. In one embodiment, the O-glycosylated recombinant therapeutic polypeptide of the invention has a molecular weight of around 65 kDa or higher. In one embodiment, the O-glycosylated recombinant therapeutic polypeptide of the invention has a molecular weight of around 100 kDa or higher. In one embodiment, the O-glycosylated recombinant therapeutic polypeptide of the invention has a molecular weight of around 150 kDa or higher.

The O-glycosylated recombinant therapeutic polypeptide of the invention may be any therapeutic polypeptide in which it is desirable to have an O-linked glycosylation sequence present.

In one embodiment, the O-glycosylated recombinant therapeutic polypeptide of the invention is an antibody or antigen binding fragment thereof.

In one embodiment, the O-glycosylated recombinant therapeutic polypeptide of the invention is an Fc protein.

In one embodiment, the O-glycosylated recombinant therapeutic polypeptide of the invention is a, Tn3 scaffold, a Darpin, a scFv, an Affibody or a domain antibody Position of the Engineered O-Linked Glycosylation Sequence The engineered O-linked glycosylation sequence can be present anywhere on the O-glycosylated recombinant therapeutic polypeptide of the invention provided that the protein is still biologically active, even if the biological activity is altered from the biological activity of the corresponding recombinant therapeutic polypeptide without the engineered O-linked glycosylation sequence. Suitable experiments to determine the effect of the engineered O-glycosylation sequence on protein structure/function will be known to the skilled person for the particular therapeutic polypeptide being used.

In order for the O-glycan to be linked to the engineered therapeutic polypeptide, target amino acids (S/T/Y) of the engineered O-linked glycosylation sequence must be conformationally accessible to the primary glycosylation enzymes (e.g. ppGalNAc-Ts). In one embodiment, the engineered O-linked glycosylation sequence must be accessible at the solvent exposed surface of the therapeutic polypeptide during post translational modification in the Golgi apparatus. The person skilled in the art will appreciate that the selection of appropriate cell lines and conditions for post translational modification may affect the efficiency of O-glycosylation, however, the selection of such cell lines and conditions to optimise the efficiency is a matter of routine optimisation.

Accessibility of the engineered O-linked glycosylation sequence can be aided by use of linkers (L1/2) which generally will have little or no 3-dimensional structure but will improve accessibility of the O-linked glycosylation sequence. In an embodiment the linker may help to encourage the structural motif to form a 'kinked' structure e.g. through the presence of Cys bridges or proline rich sequences. A linker may be present on one or both sides of the engineered O-linked glycosylation sequence:

-(L1)$_m$-(engineered O-linked glycosylation sequence)-(L2)$_n$- where m and n are independently 0 or 1. And L1 may have be identical to L2 or the two may be different. L1 and/or L2 are preferably short so as to minimally disrupt the native protein, but will vary in length to compromise for accessibility. Linkers may be between 1 and 30 amino acid residues, preferably between 1 and 10, most preferably between 1 and 5.

Suitable peptide linkers will be known to the skilled person. For example, Gly4S linkers, A/P linkers, charged linkers, PolyP and PolyA linkers. Linkers may add further structure or function, in one embodiment this could include protease cleavage sites or tags.

It is generally preferred that the engineered O-linked glycosylation sequence is not adjacent to or in close proximity to a naturally occurring residue which can be O glycosylated. (For example, if there is a Ser, Thr or Tyr in close proximity to the engineered O-linked glycosylation sequence, this might provide a secondary O-glycosylation site). As such, such a site would need to be either engineered out of the protein or the engineered O-linked glycosylation sequence would need to be positioned in a different location relative to the natural occurring residue. This may be achieved either by complete relocation of the O-linked glycosylation site or by the insertion of a suitable linker. Alternative methods exist to control this phenomenon— including use of lectin-domain truncated ppGalNAc-Ts which do not possess ability to propagate glycosylation or indeed modified saccharide incorporation which prevents lectin domain recognition/extension thereby.

Notwithstanding the above there may be instances in which additional O-glycoslation of adjacent residue is desired. In which case linkers rich in S/T or providing appropriate spacing from the instigating site to afford optimal secondary O glycosylation events.

Downstream or upstream Ser or Thr need to be distanced from the engineered glycosylation site e.g. by a distance of approximately 10 amino acids although the precise number of amino acids will vary according to the peptide and may be greater or less than this value e.g. between 5 and 15 amino acids.

The engineered O-linked glycosylation sequence may be present at any suitable position in the engineered therapeutic polypeptide. Thus, it will be understood that the engineered O-linked glycosylation sequence may be at the C-terminus of the engineered therapeutic polypeptide. The engineered O-linked glycosylation sequence may be at the N-terminus of the engineered therapeutic polypeptide. In this sense, it will be understood that the engineered O-linked glycosylation sequence may not be within the therapeutic polypeptide sequence but rather may be an extension of that sequence to either the C- or N-terminus (optionally using a linker). The engineered O-linked glycosylation sequence may be between the C-terminus and N-terminus of the engineered therapeutic polypeptide (i.e. within the engineered therapeutic polypeptide). The engineered O-linked glycosylation sequence may be near (e.g. within 10 amino acids) of the C-terminus of the engineered therapeutic polypeptide. The engineered O-linked glycosylation sequence may be near (e.g. within 10 amino acids) of the N-terminus of the engineered therapeutic polypeptide. The engineered sequence may be in between two distinct components of the therapeutic—for example between the scaffold and peptide regions of an Fc-peptide fusion.

In one embodiment, the engineered O-linked glycosylation sequence is positioned in a loop domain of the engineered therapeutic polypeptide. Such a location matches the site of natural glycosylation which usually occurs within unstructured regions of a polypeptide. Engineering methods of the art may allow initially unsuitable locations to be adopted; e.g. use of linker domains to extrude O-glycosylation sequence from globular domains.

Existing technology allows the study of proteins (e.g. using the amino acid sequence, mass spectrometry and known crystal structures) to characterise pre-existing O-glycosylation sites and/or identify those domains most suitable for introduction of an engineered O-linked glycosylation sequence.

A promising position for the engineered O-linked glycosylation sequence may therefore be arrived at by taking into account all of the above.

It will be further understood that engineering an O-linked glycosylation sequence into a therapeutic polypeptide is known in the art and, thus, additional information is available in the art regarding the position of the engineered O-linked glycosylation sequence.

In one embodiment, the O-glycosylated recombinant therapeutic polypeptide of the invention is an antibody or fragment thereof and the engineered O-linked glycosylation sequence is present in the hinge region of the antibody. Functional moieties, such as cytotoxins, may be conjugated to the antibody through such sites, e.g. to make antibody drug conjugates (ADCs).

Number of O-glycans

The recombinant therapeutic polypeptide according to the invention has been engineered to have at least one residue that is O-glycosylated.

In one embodiment, at least one engineered O-linked glycosylation sequence is glycosylated at a single position in the sequence. In another embodiment, the at least one engineered O-linked glycosylation sequence is glycosylated at multiple (e.g. 2, 3, 4 or 5) positions in the sequence.

It might be desirable to have more than one engineered O-linked glycosylation sequence. In one embodiment, the recombinant therapeutic polypeptide has e.g. two, three, four or five engineered O-linked glycosylation sequences. Where there is more than one engineered O-linked glycosylation sequence, each engineered O-linked glycosylation sequence may be the same or different.

In another embodiment more than one glycan may be present but one or more of these O-glycans may be outside the engineered O-glycosylation sequence. The propagative properties of ppGalNAc-Ts may be exploited to achieve such glycosylation patterns.

Recombinant therapeutic polypeptides of the invention may be expressed as a component of a larger expression product and subsequently truncated post-translationally. Such post-translational modification may be suitable for use where propagative glycosylation is initiated but is not limited to the engineered sequence. e.g. Fc-Peptide-S/T-Peptide-CleavageSite-GlycanMotif→Fc-Peptide-S/T-Peptide.

The Engineered O-Linked Glycosylation Sequence

The engineered O-linked glycosylation sequence may be of a defined length. The engineered O-linked glycosylation sequence should be of sufficient length to be a target for O-linked glycosylation but of a sufficiently short length so as to provide no or minimal disruption to structure/function of the protein.

The engineered O-linked glycosylation sequence may be between about 5 amino acids and 25 amino acids in length. The engineered O-linked glycosylation sequence may be at least 5 amino acids in length. The engineered O-linked glycosylation sequence may be at least 6 amino acids in length. The engineered O-linked glycosylation sequence may be up to about 7 amino acids in length. The engineered O-linked glycosylation sequence may be up to about 8 amino acids in length. The engineered O-linked glycosylation sequence may be up to about 9 amino acids in length. The engineered O-linked glycosylation sequence may be up to about 10 amino acids in length. The engineered O-linked glycosylation sequence may be up to about 11 amino acids in length. The engineered O-linked glycosylation sequence may be up to about 12 amino acids in length. The engineered O-linked glycosylation sequence may be up to about 13 amino acids in length. The engineered O-linked glycosylation sequence may be up to about 14 amino acids in length. The engineered O-linked glycosylation sequence may be up to about 15 amino acids in length. The engineered O-linked glycosylation sequence may be up to about 16 amino acids in length. The engineered O-linked glycosylation sequence may be up to about 17 amino acids in length. The engineered O-linked glycosylation sequence may be up to about 18 amino acids in length. The engineered O-linked glycosylation sequence may be up to about 19 amino acids in length. The engineered O-linked glycosylation sequence may be up to about 20 amino acids in length. The engineered O-linked glycosylation sequence may be up to about 21 amino acids in length. The engineered O-linked glycosylation sequence may be up to about 22 amino acids in length. The engineered O-linked glycosylation sequence may be up to about 23 amino acids in length. The engineered O-linked glycosylation sequence may be up to about 24 amino acids in length. The engineered O-linked glycosylation sequence may be up to about 25 amino acids in length. In some embodiments, the engineered O-linked glycosylation sequence is about 5 amino acids or about 6 amino acids in length.

In certain embodiments, the O-linked glycosylation sequence may consist of exogenous amino acids that are inserted into the naturally occurring polypeptide sequences. In other embodiments the O-linked glycosylation sequence may comprise residues within sequence of the naturally occurring polypeptide and exogenous residues, wherein the exogenous residues are inserted at such positions so as to form an O-linked glycosylation sequence as disclosed herein. In more detail, such an O-linked glycosylation sequence may be made up of both endogenous and exogenous residues, which residues may/may not be contiguous (e.g. a host sequence of . . . XXXPAAEKXXX . . . (SEQ ID NO: 42) may be modified by substitution of A for T and K for P, . . . XXXPTAEPXXX . . . (SEQ ID NO: 43)).

The engineered O-linked glycosylation sequence may be between about 5 amino acids and 15 amino acids in length. The engineered O-linked glycosylation sequence may be between about 5 amino acids and 10 amino acids in length. The engineered O-linked glycosylation sequence may be between about 5 amino acids and 6 amino acids in length.

The engineered O-linked glycosylation sequence may have a defined sequence. In this regard, O-linked glycosylation sequences are known in the art. However, the natural control of O-glycosylation is complex and there is no direct correlation between any given OLGS and the presence of O-glycosylation in all circumstances/contexts. Without wishing to be bound by theory, it appears there is a fine interplay of host environment (e.g. specific ppGalNAc-T expression, nutrient availability etc.) and complex protein features beyond the mere requirement for a free-OH presenting group in the OLGS. Nonetheless engineered O-linked glycosylation sequences characterised by the presence of Ser, Thr or Tyr in proximity to one or more Pro residues appear to lead to increased O-glycosylation as a result of the formation of kinked structures with increased accessibility to the OH group. Without wishing to be bound by theory, it appears the positions of −1 and +3 (relative to Ser/Thr) are particularly sensitive to A.A. selection (favouring certain residues), those skilled in the art will appreciate that other positions are also important to optimise and that substitutions can be both dependent and independent on other sequence positions.

The present invention provides novel O-linked glycosylation sequences that provide for particularly efficient O-glycosylation.

As such, the present invention provides novel polypeptides comprising an O-linked glycosylation sequence, wherein the O-linked glycosylation sequence comprises a sequence selected from those set forth in Table 1.

In one embodiment, the engineered O-linked glycosylation sequence comprises a sequence as set forth in Table 1. In one embodiment, the engineered O-linked glycosylation sequence consists essentially of a sequence as set forth in Table 1. In one embodiment, the engineered O-linked glycosylation sequence consists of any one of the sequences as set forth in SEQ ID NO: 2-14 in Table 1.

TABLE 1

O-linked glycosylation sequences (underlined)

| Peptide Sequence | Ref | SEQ ID NO. |
|---|---|---|
| . . . EFIAWLVKG\|AAAGGSGSTASSGSGSAT . . .<br>(\| = insertion site for o glycosylation sequences) | i0 | 1 |
| . . . <u>KNPLPTKETIEQEKQAGES</u> . . . | i1 | 2 |
| . . . <u>KNPLPTKETIEQEKQTGES</u> . . . | i1 + 10T | 3 |

TABLE 1-continued

O-linked glycosylation sequences (underlined)

| Peptide Sequence | Ref | SEQ ID NO. |
|---|---|---|
| . . . KNPLPTKETIEQEK . . . | i2 | 4 |
| . . . TXXXXXKNPLPTKEAIEQEK . . . | i1 - 11T | 5 |
| . . . KNPLPTKETIE . . . | i3 | 6 |
| . . . KNPLPTKET . . . | i4 | 7 |
| . . . PLPTKE . . . | i6 | 8 |
| . . . PLPTAE . . . | i6 + 1A | 9 |
| . . . PLPTKEP . . . | i6 + 3P | 10 |
| . . . PLPTAEP . . . | i6 dbl | 11 |
| . . . PTAEP . . . | i7 dbl | 12 |
| . . . ATAEP . . . | i8 P-1A | 13 |
| . . . PTAEA . . . |  | 14 |
| . . . AAPGPTPGP . . . |  | 15 |
| . . . AAVGATVEG . . . |  | 16 |
| . . . AADSTTPAP . . . (natural, derived from EA2 peptide) |  | 17 |
| . . . AASLPSISS . . . (natural, derived from NSP5 protein) |  | 18 |

The O-linked glycosylation sequences described in Table 1 may impart advantageous properties to the O-glycosylated recombinant therapeutic polypeptide of the invention through the properties afforded by labelling/modification of the O-glycan tag.

The inventors have shown that the presence of an engineered O-linked glycosylation sequence has the potential to increase the half-life of the O-glycosylated recombinant therapeutic protein of the invention as compared to the therapeutic protein without the engineered O-linked glycosylation sequence (see Example 2) through the presence of the O-glycan inhibiting proteolytic cleavage.

The presence of the engineered O-linked glycosylation sequence may alternatively or in addition result in a change to the hydrodynamic diameter of the O-glycosylated recombinant therapeutic polypeptide of the invention through the presence of an O-glycan tag.

The engineered O-linked glycosylation sequences described herein provide the ability to precisely target O-glycan modification of the O-glycosylated recombinant therapeutic polypeptide of the invention without having a substantial adverse effect on the host therapeutic polypeptide activity.

In another aspect, the present invention provides an O-glycosylated polypeptide comprising an O-linked glycosylation sequence, wherein the O-linked glycosylation sequence comprises a sequence selected/derived from those set forth in Table 1 and wherein the subsequent O-linked glycosylation sequence is covalently bound to an O-glycan. In one embodiment, the O-glycosylated polypeptide has the features of O-glycosylated recombinant therapeutic polypeptides of the invention as defined anywhere herein. The below discussion relating to conjugate forms of the O-glycosylated recombinant therapeutic polypeptides of the invention is equally applicable to the present O-glycosylated polypeptide.

Reagents for O-Glycosylation

The reagents for O-glycosylation typically include (i) a glycan and (ii) a catalytic transferase enzyme. Different types of (i) and (ii) are typically combined to produce different resulting glycan structures, many glycans requiring more than one type of (i) and (ii) to achieve maturity. The characteristic of the glycans afforded by a cell-type is controlled by the availability/expression of (i) and (ii). This environment can be changed by those skilled in the art. For example CHO cells typically afford Core 1 glycan structures but this may be altered by glycan starvation or catalytic transferase overexpression or knockout.

It will be understood that the catalytic transferase enzyme catalyses the O-glycosylation reaction in which transfer occurs of the glycan to the engineered O-linked glycosylation sequence comprised in the therapeutic polypeptide. It will be understood that in some circumstances the glycan may need de-protecting, epimerising and/or activation (e.g. phosphorylation/nucleotide coupling) enzymes.

In one embodiment, the glycan is GalNAc or GalNac derivatives which promote cellular uptake, such as, $Ac_4GalNAc$). GalNAc is advantageous due to its highly preferential use in O-glycan processing.

In one embodiment, the glycan is GlcNAc, fucose, xylose, galactose, sialic acid or mannose. The suitability of a particular glycan will depend on the cell line and the species it is derived from which determine the transferases present. In cell lines lacking certain transferases these may be introduced exogenously, e.g. using recombinant technology.

In one embodiment, the O-glycan is modified by the addition or substitution of a functional group. This functional group may provide a reactive group which can be used in a subsequent reaction e.g. a Click-chemistry reaction. In one embodiment, the O-glycan is labelled with an azide functional group. In another embodiment the functional group may provide direct benefit and such functional group delivers this effect. In one embodiment the O-glycan is protected so as to prevent further chain extension. Details of some successful O-GalNAc derivatives which are still receptive to a natural salvage pathway and ppGalNAc-Ts can be found (dx.doi.org/10.1021/cb200511t)

Labelling of the one or more O-glycans may be carried out using any suitable method. For example, azide may be incorporated into the one or more O-glycans of the modified polypeptide by using glycan biosynthetic pathways of the cell, such as the sialic acid pathways for converting mannose into NANA (e.g. feeding ManNAz will generate azide labelled sialic acid residues). A similar approach can be used for intermediaries of the GalNAc (or GlcNAc) pathways. In some embodiments, an azido analogue of GalNAc, such as N-azidoacetylgalactosamine (GalNAz), or an azido analogue of GlcNAc, such as N-azidoacetylglucosamine (GlcNAz), may be added to the cell culture medium (tetra acetylated forms). In such embodiments, the cell incorporates the azido-containing residues into one or more O-glycan tags engineered into therapeutic polypeptide.

In one embodiment, azide labelling may be carried out by adding azide-containing compounds to the cell culture medium.

In another embodiment azide-containing precursors, such as $Ac_4GalNAz$ or $Ac_4GlcNAz$, may be added to the cell medium. Such substrates are processed via the cell's salvage pathways, which is desirable because they have greater specificity for O-glycan processing and therefore result in better cell-growth and protein quality/yield.

In one embodiment, the derivatised glycan is $Ac_4GalNAz$. Accordingly, in some embodiments, at least 150 µM, at least 200 µM, at least 250 µM, at least 300 µM, at least 350 µM, at least 400 µM, at least 450 µM, at least 500 µM, at least 550 µM, at least 600 µM, at least 650 µM, at least 700 µM, at least 750 µM, at least 800 µM, at least 850 µM, at least 900 µM, at least 950 µM, at least 1000 µM, at least 2000 µM, at least 3000 µM, at least 4000 µM, or at least 5000 µM $Ac_4GalNAz$ is added to the cell culture medium.

In one embodiment, the catalytic transferase enzyme is polypeptide N-acetylgalactosaminyltransferase.

In one embodiment, the catalytic transferase enzyme is a member of the ppGalNAc transferase family e.g. ppGalNAc-T2. Other GalNAc transferase enzymes include GalNAc-T4, GalNAc-T7 and GalNAc-T10. These catalytic transferase enzymes may be modified e.g. lectin domain deleted or lectin domain modified. These catalytic transferase enzymes may be exogenous or endogenous. Depending on the desired activity they may be either overexpressed or knocked-out.

Cell-line engineering and cell-culture conditions are both considered to relate to optimisation of the method. Where optimisation is to improve the expression of recombinant protein with high, homologous yield of modified sugar incorporated into the protein.

In one embodiment, the culture conditions and feed can be manipulated in order to encourage/force O-glycosylation to proceed via the salvage pathway rather than via the classical Leloir/de novo pathway. The use of the salvage pathway provides for higher levels of homogeneity amongst the O-glycosylated therapeutic peptides produced. It is possible to force the reaction via the salvage pathway by a number of means. Starving the cells of glucose can deprive the classical pathway of substrate and activate the salvage pathway. In another embodiment promoting the salvage pathway may be achieved by knockout or inhibition of the enzymes responsible for linking the classical to the salvage pathway (e.g. isomerase enzymes such as GALE). In another embodiment promoting the salvage pathway may be achieved by overexpressing RDSs of the salvage pathway, including but not limited to host proteins (e.g. transporter, phosphorylase and uridyl transferase enzymes).

Elongation of Sugar Structure

In one embodiment, the introduced O-glycan allows for elongation of the glycan structure. Elongation of the glycan structure may produce common mucin-type glycan structures (such as Core 1) which may or may not be fully/partially sialidated. Alternatively, the introduced O-glycan may be modified to incorporate a blocking group to prevent elongation or to promote the formation of specific glycan structures. e.g. to prevent maturation of Tn antigen into a Core 1 structure or to prevent sialidation of Core 1 epitopes (from modified GalNAc or Gal feed).

In another embodiment, if prevention of elongation of glycan is desired, the cellular enzymes may be engineered so that elongation is prevented. For example by knockout of sialic acid transferases (and other specific transferases). Alternatively control may be exercised over the cell culture medium so as not to facilitate elongation of the sugar structure by for example reducing glucose feeding in order to divert the use of any sugars by the cell to maintenance and growth rather than to glycan maturation. Such methods are well known to the person skilled in the art.

It is known that expression conditions (cell environment, e.g. resources/stresses and cell heritage, e.g. cell-type/species) result in different mature O-glycan structures, e.g. CHO cells fed with glucose media favourably incorporate disialidated Core 1 mucin-type O-glycans. The person skilled in the art would be aware that different cell culture environments can be adapted and/or cell lines engineered to produce different O-glycan structures that can be incorporated onto the engineered O-glycosylation sequence. It will also be appreciated that different primary transferases (e.g. ppGalNAc-Ts from different strains or species) may elicit different sequence recognition and other early events (such as propagation). It is also expected that cell-lines/conditions may be engineered for other purposes to build on protein functionality (e.g. improve amidation or limit N-glycosylation).

O-Glycosylated Recombinant Therapeutic Polypeptide Conjugate

In still another aspect, a further molecule can be attached to the O-glycan to form an O-glycosylated recombinant therapeutic polypeptide conjugate. The present invention thus provides an O-glycosylated recombinant therapeutic polypeptide conjugate comprising an O-glycosylated recombinant therapeutic polypeptide as defined anywhere above, wherein a further molecule M is covalently linked to the O-glycan.

In still another aspect, a further molecule can be attached to the O-glycan to form an O-glycosylated recombinant therapeutic polypeptide conjugate comprising the formula:

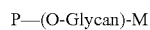

P—(O-Glycan)-M where P represents the engineered recombinant therapeutic polypeptide and M represents a molecule desirable to be attached to P. The O-glycan thus acts as a linking group between P and M.

In still another aspect, the present invention provides a method for producing an O-glycosylated recombinant therapeutic polypeptide conjugate comprising the formula:

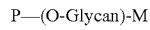

P—(O-Glycan)-M where P represents the engineered recombinant therapeutic polypeptide of the invention and M represents a molecule desirable to be attached to P. The method comprises:
(i) providing an O-glycosylated recombinant therapeutic polypeptide of the invention;
(ii) and reacting the O-glycan with M so as to covalently link M to the O-glycan.

It will be understood that the O-glycan must have a reactive group capable of reacting with the reactive group of M so as to link M and the O-glycan. Such linkages may be formed through Click chemistry reactions. Click chemistry provides excellent selectivity, efficiency and biorthogonal compatibility (see 10.1039/B613014N for some general Click chemistries). In one embodiment, the reacting comprises an azide-alkyne coupling reaction (see 10.1021/ar200148z for an example of Cu-free Click as a bioorthogonal reaction).

Other suitable coupling reactions for the reacting step include those known in the art of bioconjugation such as nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). For participation in a coupling reaction it is desirable for reactive groups to be present such as those listed below:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to, e.g., esters, ethers, aldehydes, etc.
(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be, for example, converted to disulfides or reacted with acyl halides;
(h) amine or sulfhydryl groups, which can be, for example, acylated, alkylated or oxidized;
(i) alkenes, which can undergo, for example, cycloadditions, acylation, Michael addition, etc; and
(j) epoxides, which can react with, for example, amines and hydroxyl compounds.

M may comprise any conjugable molecule; e.g. another therapeutic polypeptide, an Fc domain, a cytotoxin, a label e.g. a fluorophore, a lipid, a small molecule e.g. PEG, or a nanoparticle.

It will be understood that M will need to have a reactive group (e.g. an alkyne group) suitable for participation in the coupling reaction with the O-glycan. The addition of a reactive group such as alkyne to the molecule M is considered to be within the ability of the skilled person.

Conjugation may involve the use of a crosslinker. Preferred crosslinking reagents are derived from various zero-length and non-zero-length (e.g. PEGx spacers), homo-bifunctional, and hetero-bifunctional crosslinking reagents. Preferred homo- and hetero-bifunctional reagents contain two identical or two dissimilar sites, respectively, which may be reactive for azide, amino, sulfhydryl, guanidino, indole, or nonspecific groups etc. and generally allow for the use of a wider range of potential chemistries at the site of the O-glycan.

In some cases, it might be necessary to first react M with a linker group in order to provide the necessary reactive group for coupling M to the O-glycan, for example:
Step 1: M'+maleimide-linker-alkyne→M'-linker-alkyne
Step 2: M'-linker-alkyne+P—(O-glycan)→P—(O-glycan)-linker-M In other cases, it might be necessary to first react P—(O-glycan) with a linker group in order to provide the necessary reactive group for coupling the P—(O-glycan) to M through the linker, for example:
Step 1: P—(O-glycan)'+alkyne-linker-maleimide→P—(O-glycan)'-linker-maleimide
Step 2: P—(O-glycan)'-linker-maleimide+M)→P—(O-glycan)-linker-M Whilst it is envisaged that it will be preferable to avoid the use of linkers through the use of different GalNX feeds, the use of linkers potentially allows for an increase in yield and efficiency as cells do not need to process feed non-natural glycans. The use of linkers may also provide advantages in being able to conjugate during either biopurification or co-purification.

In one embodiment, P comprises an antibody and M comprises a cytotoxin such that P—(O-glycan)-M represents an antibody-drug conjugate (ADC). In one embodiment, more than one engineered glycosylation sequence is present in the O-glycosylated therapeutic polypeptide such that the ADC has the formula P—[(O-glycan)-M]$_z$ where z>1. z may be about 2, about 4, about 6 or about 8.

As described above, the O-glycosylated recombinant therapeutic polypeptide of the invention may be used as a substrate for further reactions, such as chemical synthesis reactions. For example, the O-glycosylated recombinant therapeutic polypeptide of the invention may be used in Click chemistry reactions.

As used herein, the term "Click chemistry" is used to refer to a class of reactions that join substrates with high thermodynamic driving force and little byproduct/waste nor reversibility. Click chemistry reactions can provide high yields of reaction product in a "one pot", "copper free" reaction, which can take place quickly and with high reaction specificity. The biocompatibility of Click chemistry is particularly important in the industry and provides further advantages including mild reaction conditions and low recipient toxicity. The specificity and selectivity of Click reactions designed to occur at engineered sites prevents off site host reactivity.

Click chemistry may be used to conjugate an azide functional group with an alkyne functional group. This classically involves a Huisgen 1,3-dipolar cycloaddition catalysed by Cu(I)-CuAAC (Cu-catalysed Azide Alkyne Cycloaddition). More recently this has matured to involve Cu-less reactions which are more biocompatible due to reduced cytotoxicity. Examples include Strain Promoted Azide-Alkyne Cycloaddition (SPAAC) which is a concerted [3+2] cycloaddition of almost equal reactivity and stability to CuAAC. Further reactive Click Chemistries are available and newly discovered Click Chemistries are also included in the scope of the invention (see dx.doi.org/10.1021/cr400355w for good demonstration of different conjugation efficiencies).

For example, in vivo Click reactions, as a possible drug delivery mechanism, may rely on higher reactive chemistries such as tetrazine-TCO coupling (see dx.doi.org/10.1021/cr400355w). In another embodiment the scope of the invention includes any group which can be incorporated in the O-glycosylation sequence via enzymatic metabolic processes; be that natural host enzymes, or non-natural enzymes introduced or engineered in anticipation of altered properties. E.g non-Click chemistries or already functional groups. Such implemented design would require novel enzymes.

It will be understood that an O-glycosylated recombinant therapeutic polypeptide of the invention that is labelled with an azide moiety may be suitable for Click Chemistry reactions. For example, an O-glycosylated recombinant therapeutic polypeptide of the invention may be modified by the attachment of an azide functional group to the one or more O-glycans. Such a protein may undergo a Click chemistry reaction with a substrate containing an alkyne functional group. Such conjugation is highly specific and irreversible.

Thus, an O-glycosylated recombinant therapeutic polypeptide of the invention that is labelled with an azide functional group may be reacted with a substrate containing an alkyne functional group. The substrate containing an alkyne functional group may be any substrate that is desirable to conjugate to the O-glycosylated recombinant therapeutic polypeptide of the invention. Alternatively, this arrangement can be reversed and the O-glycan may present the free alkyne and the substrate present the free azide.

Host Cell Line

It will be understood that any suitable host cell may be used for expression of the engineered therapeutic polypeptide. In some embodiments, the engineered therapeutic polypeptide is expressed in a mammalian cell line. For example, the engineered therapeutic polypeptide may be expressed in a CHO cell line or a HEK cell line. In some embodiments, a CHO cell line is used. In other embodiments a HEK cell line such as HEK293F or HEK293T is used.

A particularly suitable cell line would be CHO IdID cells which contain a knockout of the epimerase responsible for the de novo synthesis of UDP-GalNAc and thus favour the salvage pathway.

Another particularly suitable cell line would be HEK cells which contain a knockout of the UDP-Galactose-4-Epimerase (GALE) gene. For instance, HEK293T GALE KO cells as described in Termini et al. (2017) PLoS ONE 12(6): e0179949.

In embodiments where the cell line is not a mammalian cell line other production systems (e.g. insect cell, E. coli) may be used. It will be appreciated that these may require exogeneous enzyme co-expression to transform such cell types into a suitable O-glycan affording system. Such methods are well known in the art.

It will be understood that the host cell line may be transiently or stably transfected with recombinant vector.

Disease Treatment or Prevention

The present invention provides a method of treating or preventing disease in a patient, the method comprising administering to the patient any of the above mentioned products of the invention.

The present invention provides any of the above mentioned products of the invention for use as a medicament.

In another aspect, the present invention provides second medical uses of the above mentioned products of the invention.

In another aspect, the present invention provides pharmaceutical compositions comprising any of the above mentioned products of the invention.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In the context of the present disclosure other examples and variations of the devices and methods described herein will be apparent to a person of skill in the art. Other examples and variations are within the scope of the disclosure, as set out in the appended claims.

EXAMPLES

Example 1: Development of O-Linked Glycosylation Sequences

A short amino acid sequence from Thymosin-β4 protein was found to result in O-glycosylation when present N-terminally as a Thymosin-β4:linkerFc-fusion protein. The Thymosin-β4 amino acid sequence in the fusion protein is as follows:

(SEQ ID NO. 1)
GSDKPDMAEIEKFDKSKLKKTETQE<u>KNPLPSKETIEQEKQAGES</u>

The last 19 amino acids of the Thymosin-β4 sequence (indicated by underlining) were then incorporated into a GLP-1:Fc-fusion protein, and the amount of O-glycans present was measured. The molecule was then optimised. Optimisation included reducing the number of amino acid residues, and exchange of amino acid residues. The optimised sequences and their results are shown in Table 2 and the glycosylation profiles of wild-type TB4, a fusion protein containing the sequence PLPTAE (SEQ ID NO: 9) and a fusion protein containing the sequence ATAEP (SEQ ID NO: 13) are shown in FIG. 1.

As can be seen from Table 2 and FIG. 1, a number of the sequences resulted in high O-glycosylation, with the fusion proteins predominantly containing a single glycan (e.g. PLPTAE (SEQ ID NO: 9)) or multiple glycans (e.g. ATAEP (SEQ ID NO: 13)) but that the effect of alterations to the O-linked glycosylation site are not entirely predictable.

TABLE 2

O-glycosylation of GLP-1: Fc fusion proteins
(% of O-glycosylated molecules with a
glycan anywhere on the molecule)

| Peptide Sequence* | SEQ ID NO. | % O-glycan |
|---|---|---|
| . . . KGAAAGGSGSTASSGSGSAT . . . | 19 | <10 |
| . . . KG_KNPLPTKETIEQEKQAGES_AAAGSSGSGSAT . . . | 20 | 100 |
| . . . KG_KNPLPTKETIEQEKQ_TGESAAAGSSGSGSAT . . . | 21 | 100 |
| . . . KG_KNPLPTKETIEQEK_GSTASSGSGSAT . . . | 22 | 96 |
| . . . KG_KNPLPTKETIEQEK_GSTASSGSGSAT . . . | 23 | 96 |
| . . . KG_KNPLPTKEAIEQEK_GSTASSGSGSAT . . . | 24 | 100 |
| . . . KG_KNPLPTKETIEQEK_GAAASSGSGSAT . . . | 25 | 100 |
| . . . KG_KNPLPTKETIE_GSTASSGSGSAT . . . | 26 | 91 |
| . . . KG_KNPLPTKET_GSTASSGSGSAT . . . | 27 | 92 |
| . . . KG_KNPLPTKE_GSTASSGSGSAT . . . | 28 | 71 |
| . . . KG_PLPTKE_GSAT . . . | 29 | 60 |
| . . . KG_PLPTAE_GSAT . . . | 30 | 93 |
| . . . KG_PLPTKE_PGSAT . . . | 31 | 97 |
| . . . KG_PLPTAE_PGSAT . . . | 32 | 94 |
| . . . KG_PTKE_RGSAT . . . | 33 | 0 |
| . . . KG_PTAE_PGSAT . . . | 34 | 100 |
| . . . KG_ATAE_PGSTASSGS . . . | 35 | 96 |
| . . . KG_PTAE_AGSTASSGS . . . | 36 | 76 |
| . . . KGAA_PG_PT_PGPGSTASSGSGSAT . . . | 37 | 100 |
| . . . KGAAVGA_TV_EGGSTASSGSGSAT . . . | 38 | 14 |
| . . . KGAADST_T_PAPGSTASSGSGSAT . . . | 39 | 100 |
| . . . KGAAS_LP_SISSGSTASSGSGSAT . . . | 40 | <10 |

Example 2: O-Glycan Characterization

A selection of the sequences from Example 1 were then further characterised.

Glycoforms and Levels of Sialidation

Figure 2:
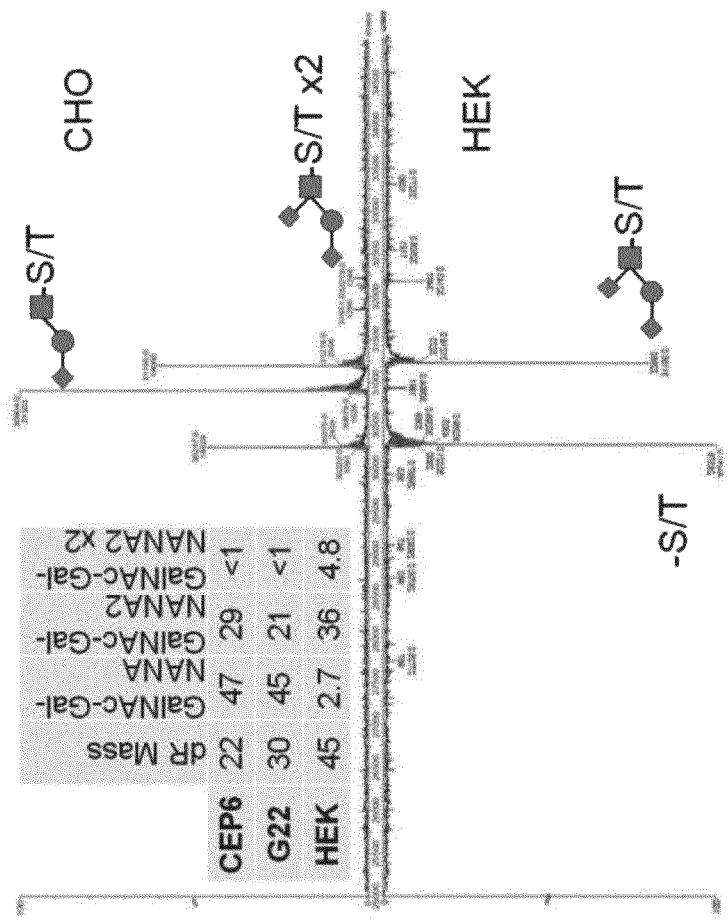
FIG. 2 shows characterisation of different glycoforms by mass spectrometry.

Mass spectrometry was used to determine the glycoforms present and levels of sialidation in the fusion proteins when they were expressed in either CHO or HEK cells. The results are shown in FIG. 2.

SEC-MALS

Figure 3:
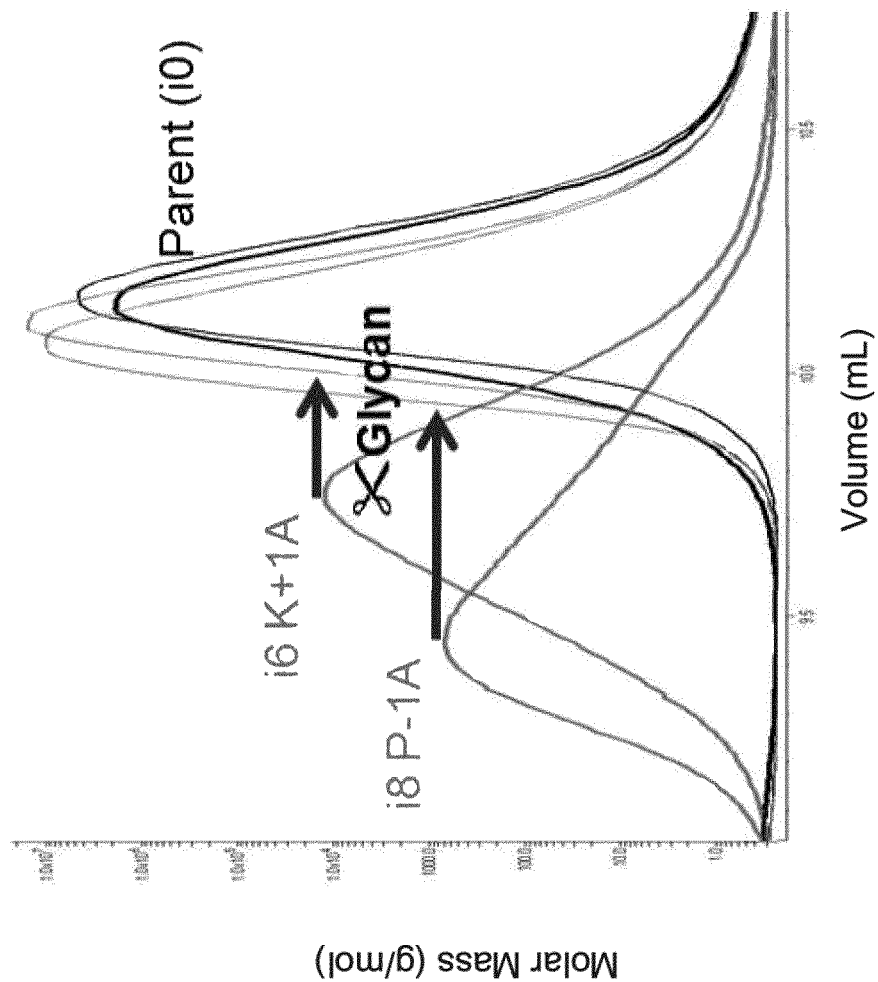
FIG. 3 shows the effect of O-glycosylation on retention time using SEC-MALS.

The physicochemical properties of the fusion proteins were measured using SEC-MALS. The results are shown in FIG. 3.

Rodent PK Study

Figure 4:
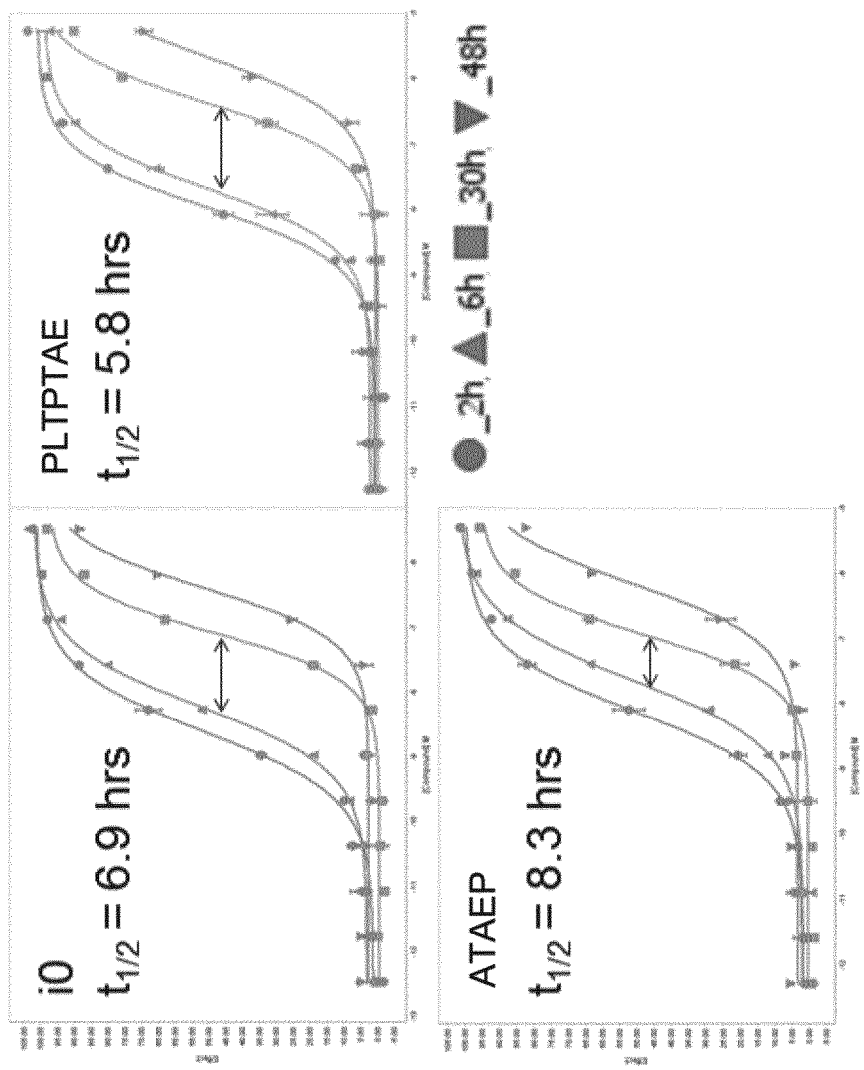
FIG. 4 shows the results of a half life study in a rodent PK model measured by HTFR cAMP assay in hGLP-1R cells.

The pharmacokinetic properties of the fusion proteins were measured in rats using the HTFR cAMP assay with hGLP-1R cells to determine the construct half-life. As can be seen from FIG. 4, a fusion protein containing the sequence PLPTAE (SEQ ID NO: 9) had a slightly lower half-life than wild-type, and a fusion protein containing the sequence ATAEP (SEQ ID NO: 13) had a longer half-life than wild-type.

Peptide Activity

Figure 5:
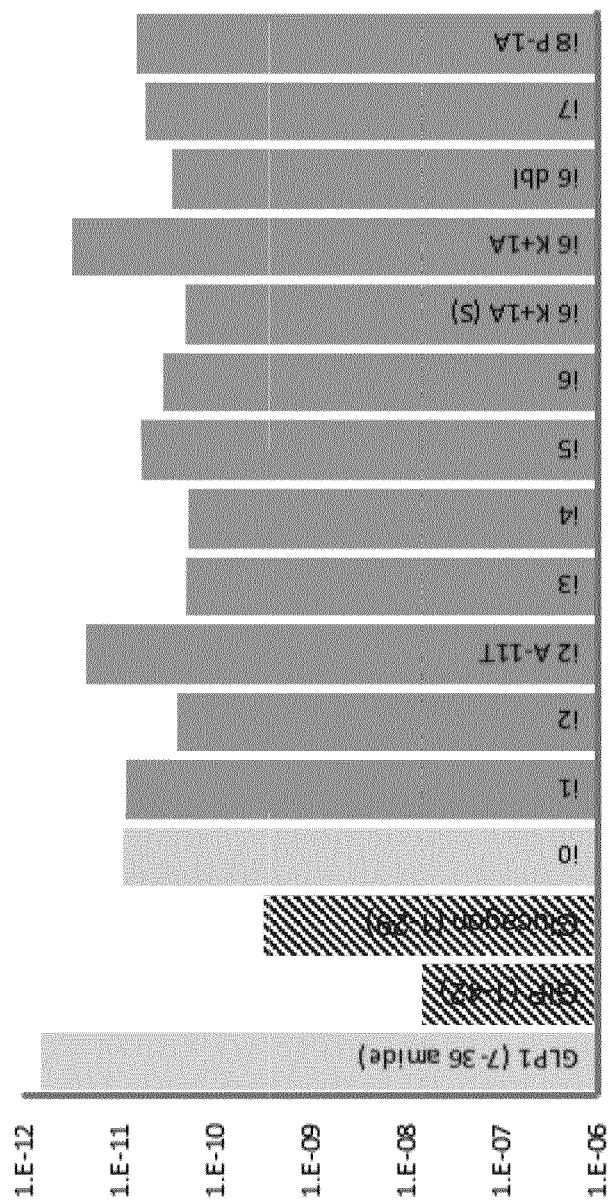
FIG. 5 shows peptide activity against hGLP-1R.

Finally, the peptide activity on a number of the fusion proteins was measured. The results are shown in FIG. 5. As can be seen from the figure, the presence of the altered sequences has a low impact on function.

Example 3: Azide Labelling of an O-Glycan-Tagged Peptide

Figure 6:
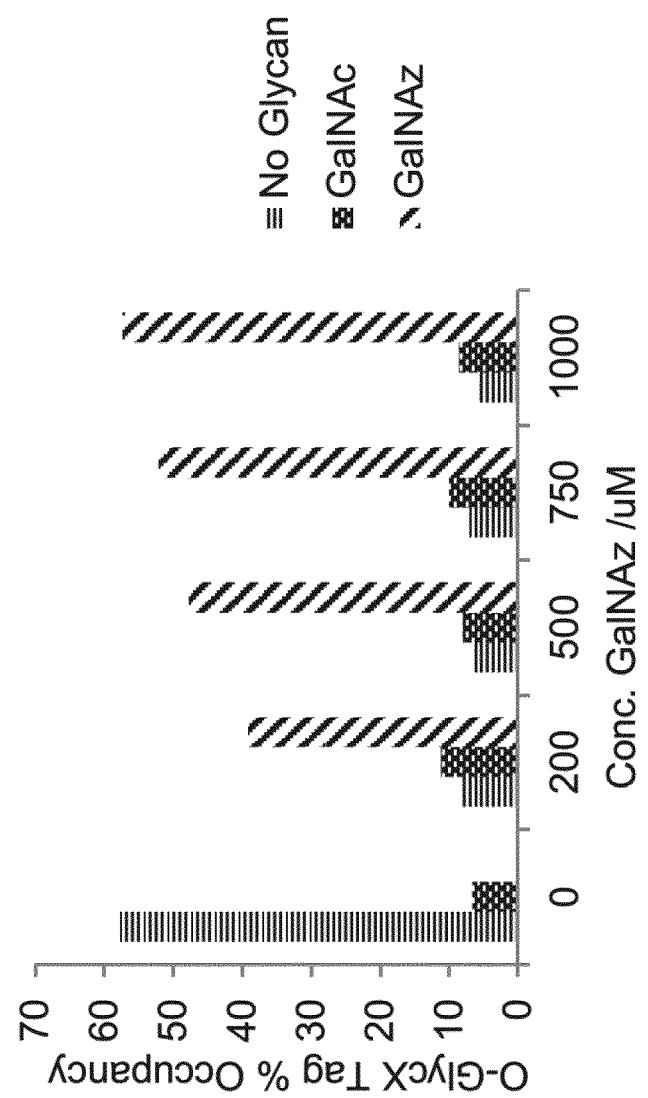
FIG. 6 shows increasing concentration of GalNAz in feed starved, transient expressions correlates with label incorporation.

CHO cells transiently expressing a recombinant Fc protein with a PTAEPG (SEQ ID NO: 41) 0-glycosylation sequence were cultured at 37° C. for 72 hours in culture medium containing $Ac_4GalNAz$ (and only passage residing glucose, no supplementation). The percentage occupancy of the glycans GalNAc and GalNAz in cells cultured in increasing concentrations of $Ac_4GalNAz$ was measured and the results are shown in FIG. 6. As can be seen from FIG. 6, $Ac_4GalNAz$ feeding of CHO cells transiently expressing the fusion protein yields high levels of GalNAz incorporation.

In a further experiment, cells were incubated under different environmental conditions (time to harvest and temperature) and the O-glycan profile measured. Here observed is a means to further optimise the culture process such that labelled sugar is favourably incorporated. This is likely due to cells favouring the use of the salvage pathway in a glucose-starved growth state. Cells starved of glucose and labelling agent poorly express O-glycans indicating an essential role of nutrient availability to glycan processing (diversion of glucose to essential processes expected). Moreover, these results demonstrate that it is feasible to modulate GalNAz labelling by changing the cell culture conditions, such as the temperature. We also observe the preference of CHO cells to using the salvage pathway (under certain conditions—for example glucose starvation). And also the characteristic expression patterns of CHO cells (e.g. a preference for Core 1 expression only and this is limited to un-sialidated forms when the cell is under stress by glucose withdrawal).

Example 4: Click Chemistry: Addition of Alkyne Group

Following the successful incorporation of a GalNAz label onto the Fc protein, experiments were then conducted to "Click" a moiety containing an alkyne group (e.g. DBCO or DIBO) onto the GalNAz-labelled protein.

Figure 7:
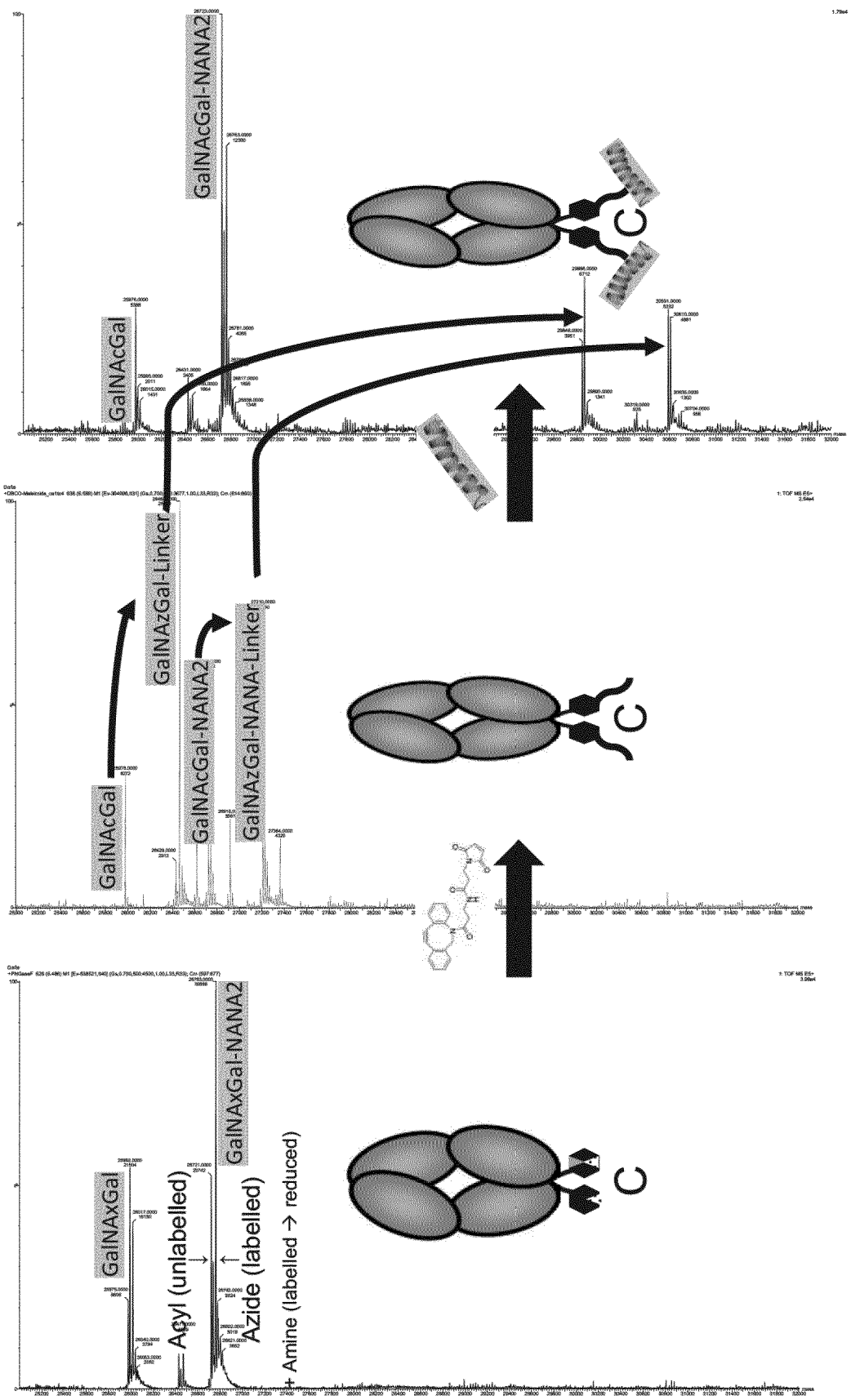
FIG. 7 shows the results of using click chemistry to conjugate functional groups through the incorporated O glycan tags.

In the first panel of FIG. 7 there are three peaks, which correspond to Fc with no glycan incorporated, Fc with O-glycan ("unlabelled") and Fc with GalNAz incorporated ("labelled").

The second panel of FIG. 7 shows the peaks following addition of a linker and the third panel shows the peaks following addition of a moiety containing an alkyne group. In addition to the peaks corresponding to Fc not containing GalNAz and GalNAz-labelled Fc, there is also a peak corresponding to GalNAz-labelled Fc that has "Clicked" with the alkyne group of the moiety containing an alkyne group.

Example 5: Click Chemistry: Conjugation with Bifunctional Crosslinkers

Heterobifunctional Crosslinkers; Fc-Scaffold+Peptide Conjugation

Conjugation involved the use of heterobifunctional crosslinkers (DBCO-Maleimide and DBCO-PEG4-Maleimide). A maleimide complementing peptide (presenting free-thiol) was used alongside SPAAC in a one-pot fashion without purification (1:4:16 azide/alkyne-maleimide/free-thiol). This provided a good level of efficiency of conjugation. Homobifunctional Crosslinkers; Fc-Scaffold Dimer Conjugation involved dimerisation of Fc-scaffold presenting O-GalNAz via a homobifunctional crosslinker (DBCO-PEG4-DBCO). SPAAC successfully produced conjugated species even with an excess of linker and no immobilisation.

Example 6: Azide Labelling of an O-Glycan Tagged Peptide in CHO K1 GALE KO

Figure 8A:
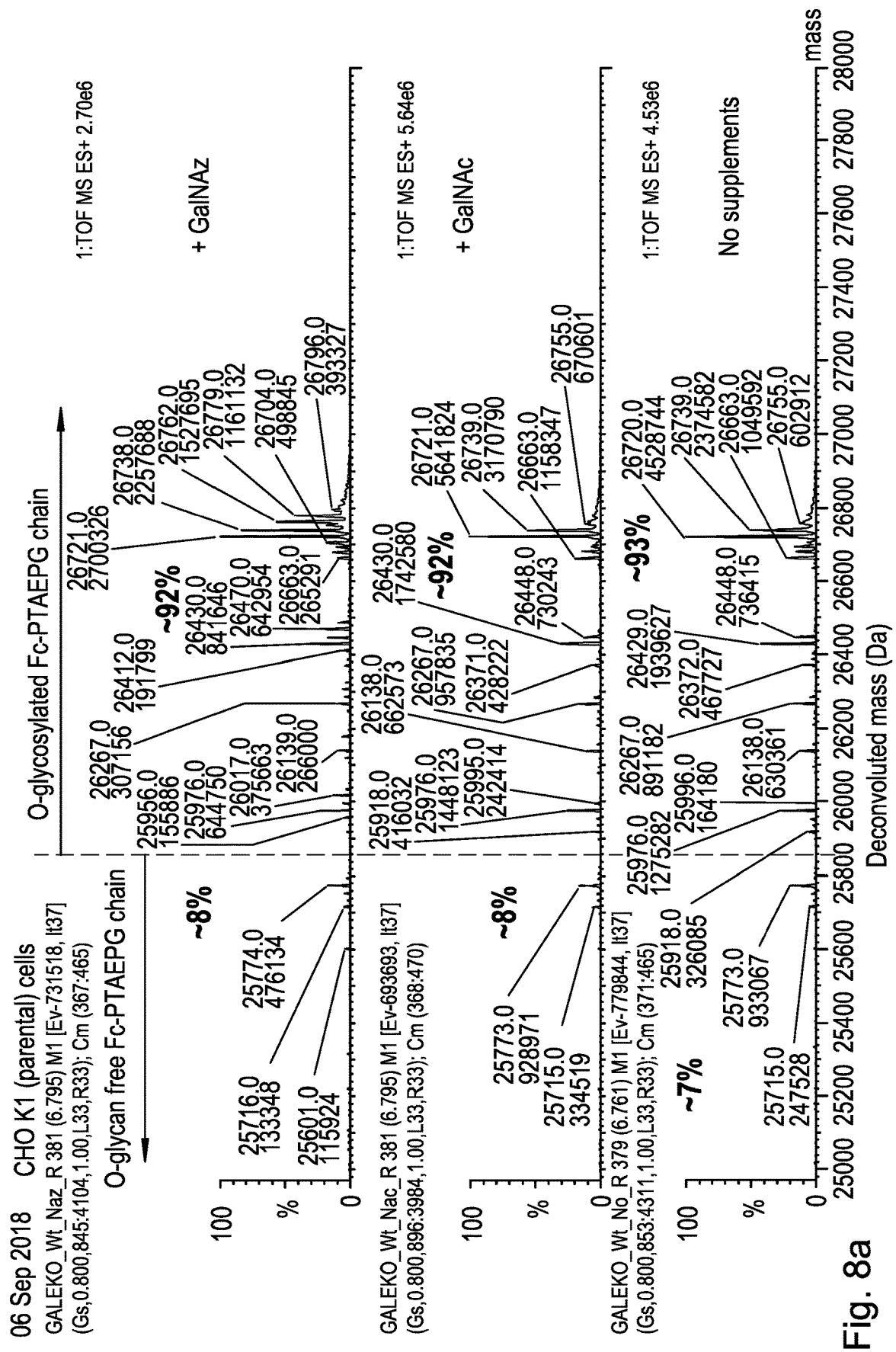
FIG. 8 O-glycosylation profile of Fc-PTAEPG expressed in either CHO K1 (a) or CHO K1 GALE KO (b) in the presence or absence of N-acetyl galactosamine (GalNAc) and its derivatives. Relative amounts of O-glycan free and O-glycosylated species were calculated based on the MS peak intensities.
Figure 8B:
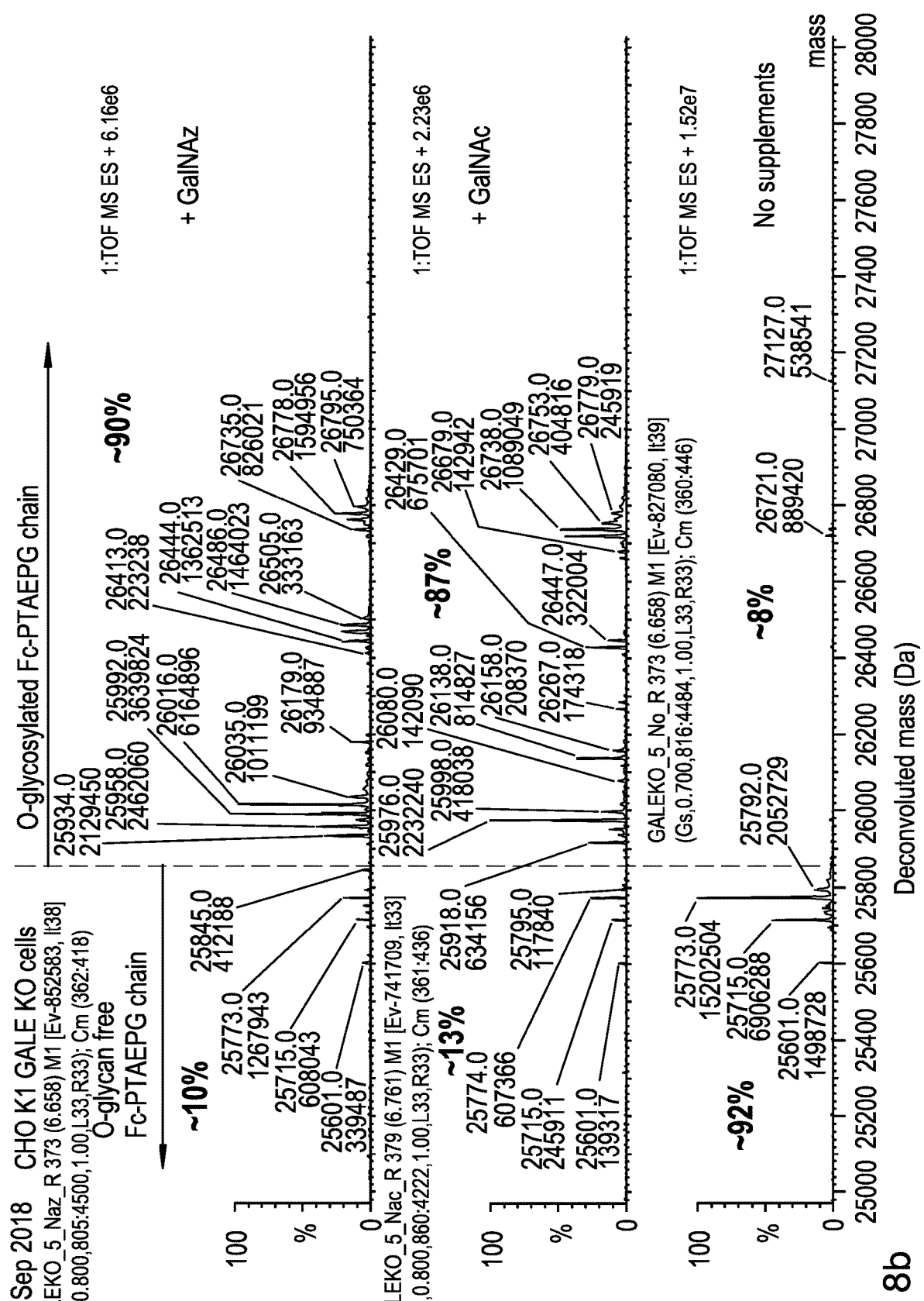

CHO K1 GALE knockout cells were generated using the CRISPR/Cas9 gene editing technique. CRISPR guide RNAs (gRNAs) were constructed targeting the CHO UDP-glucose 4-epimerase gene (GALE; NW_003622938.1) Briefly, three gRNAs were co-transfected into CHO K1 cells grown in HAM's F12 media—5'-ccacacggtactggagctgc-3' (Exon2), 5'-gtactggagctgctggaggc—3' (Exon2) & 5'-cggcgggtccag-gaactgac—3' (Exon3), this plasmid also expresses a RFP reporter gene for the identification of CRISPR transfected cells. RFP-positive cells were sorted into single cell clones by FACS-based sorting. Clones were then screened for GALE KO by western blot analysis. CHO K1 GALE KO Fc-PTAEPG-expressing cells were generated by transduction of CHO K1 GALE KO cells with Fc-PTAEPG-containing lentivirus particles. Fc-PTAEPG lentiviral particles were generated using a commercially available 3rd generation integrating lentiviral vector. The Fc-PTAEPG protein was cloned into the expression cassette of a lentiviral vector co-expressing a gene encoding resistance to the mammalian selection agent puromycin. Both genes were under the control of the high-expressing cytomegalovirus (CMV) promoter. Pools of Fc-PTAEPG-expressing cells were isolated after cell selection in 10 µg/ml puromycin for 2 weeks. For labelling of Fc-PTAEPG protein CHO K1 Fc-PTAEPG cells were incubated in serum-free media containing no supplements or 75 µM of either GalNAc or GalNAz for 4 days. The CHO K1 wt Fc-PTAEPG cell pools generated as above served as a control. Proteins were purified from the cell medium. The proteins were de-N-glycosylated using PNGaseF followed by disulphide reduction and analysed by LC-MS using UPLC and OToF Mass Spectrometry (FIG. 8).

Figure 9A:
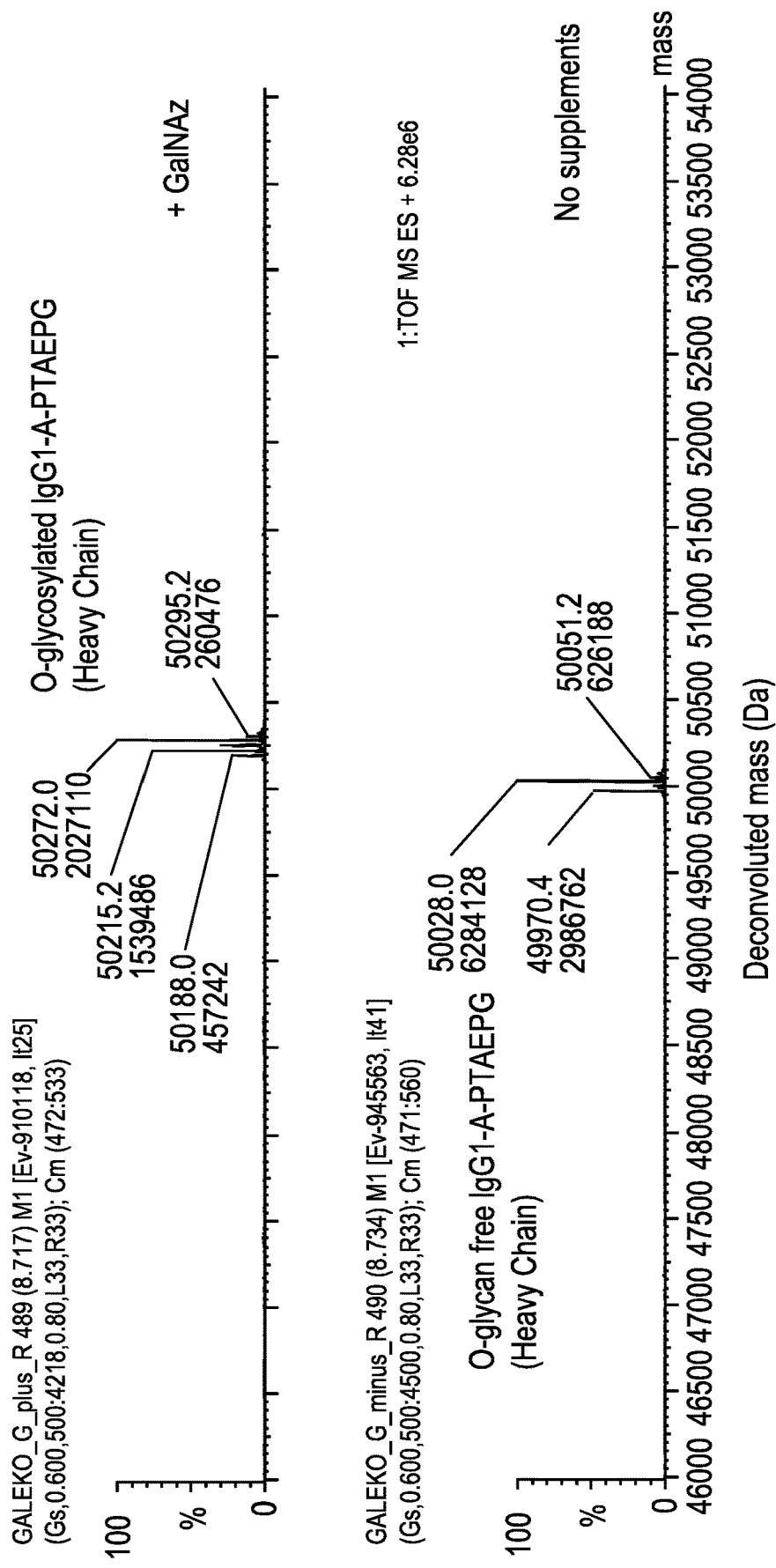
FIG. 9 O-glycosylation profile of IgG1-A-PTAEPG (panel a) and Fc-PTAEPG (panel b) expressed in HEK293F GALE KO in the absence or presence of 50 µM Ac4GalNAz, followed by copper-free "Click" chemistry addition of AF488-DBCO reagent to GalNAz-labelled Fc (panel b)
Figure 9B:
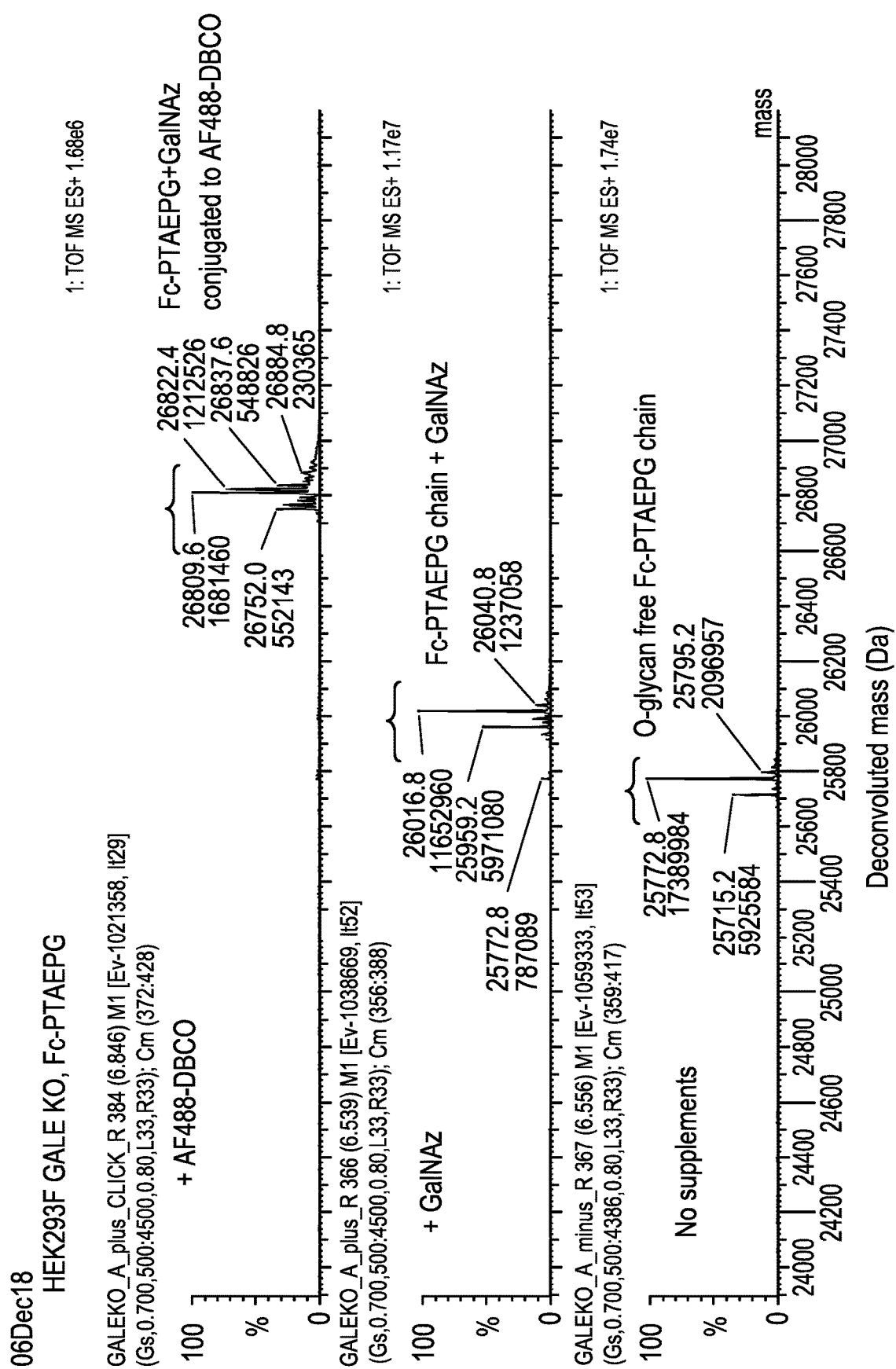

Example 7: Azide Labelling of an O-Glycan Tagged Peptide in the Context of an Fc and IgG Fusion in HEK 293F GALE KO The HEK293F cell line is a clonal variant of HEK293 cells that grows in suspension culture and can achieve high cell densities and high recombinant protein yields after transient transfection. Achieving efficient CRIPSR/Cas9-mediated gene knockouts is challenging in suspension cultures. Thus, the following procedure, which ensures high levels of gene knockout, was devised. HEK293F cells were rendered adherent by culturing the cells in FreeStyle 293 expression media (Thermo Fisher) supplemented with 10% foetal bovine serum (FBS) in poly-D-lysine-treated cell culture plates. Adherent HEK293F cells were then transfected with CRISPR/Cas9 plasmids targeting the human UDP-glucose 4-epimerase gene (GALE; NC_000001.11) Briefly, two gRNAs were co-transfected into HEK293F cells—5'-gtactggagctgctggaggc—3' (Exon3) & 5'-cggcgggtccaggaactgac—3' (Exon4), this plasmid also expresses a RFP reporter gene for the identification of CRISPR transfected cells. RFP-positive cells were sorted into single cell clones by FACS-based sorting. Clones were screened for GALE KO by western blot analysis. After HEK293F GALE KO clones were identified the cells were re-adapted to suspension culture to generate the final suspension HEK293F GALE KO cell line. Rapid re-adaption to suspension culture was achieved by sequentially lowering the FBS concentration of the culture medium from 10%, 5%, to 2% over a period of one week after which the cells were directly seeded into shaking flask cultures at 1×106 cells/ml in FreeStyle media for routine culture. HEK293F GALE KO cells were transiently transfected with plasmids expressing either an Fc or an IgG protein harbouring a PTAEPG (SEQ ID NO:41) O-glycosylation sequence. Cells were cultured at 37° C. for 5 days in the FreeStyle culture medium conditionally supplemented with 50 µM Ac4GalNaz Proteins were purified from the cell medium and the GalNAz containing proteins were subjected to click-chemistry reaction with using 2-fold molar access of AF488-DBCO (Click Chemistry Tools #1278) in PBS at room temperature. Proteins were analysed using LC-MS as described in example 6 (FIG. 9*a* and FIG. 9*b*)

Figure 10:
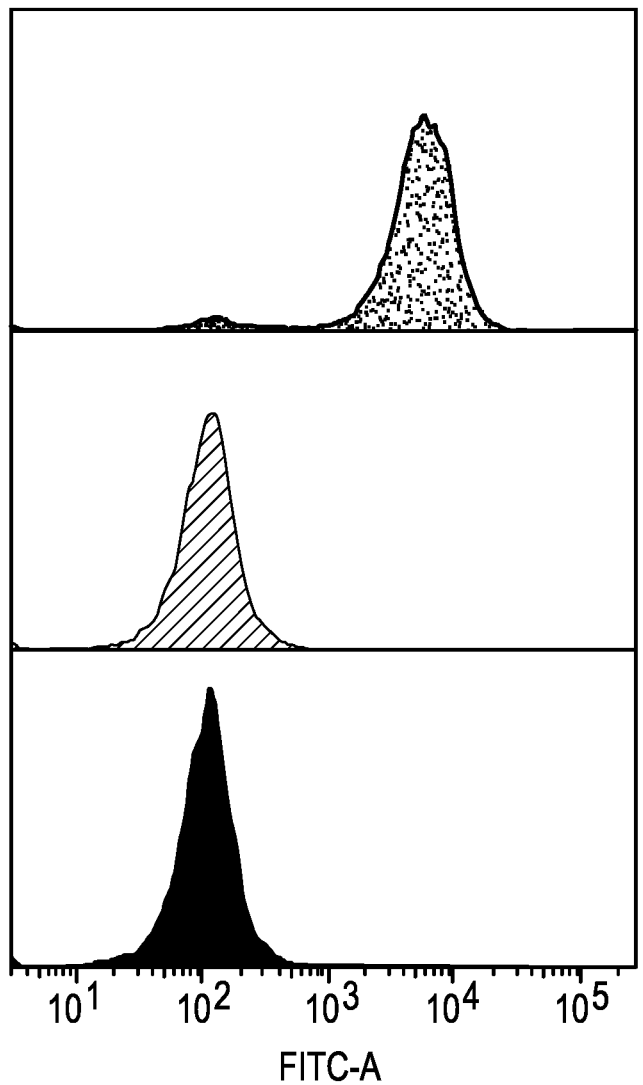
FIG. 10 FACS analysis of cells positive (+A) and negative (−A) for receptor A with the IgG1 specific for receptor A (IgG-A-PTAEPG), generated using HEK293F KO cell line in the presence of GalNaz and labelled with AF488 using click-chemistry. Fc-PTAEPG labelled in the similar way was used as a negative control

For FACS analysis a human IgG1 antibody targeting cell receptor A (IgG-A-PTAEPG) was used. Immunofluorescent staining of cells for FACS analysis was performed as follows: Non-specific binding on cells expressing receptor A was blocked by incubating the cells in a solution of Fc receptor blocking mAbs and 10% FBS. Blocked cells were then incubated with receptor A-specific IgG1-A-PTAEPG-AF488 generated by "Click" chemistry or control Fc-PTAEPG-AF488 generated by click chemistry at a concentration of 10 μg/ml for 20 mins. Excess stain was washed off and FACS analysis of receptor expression on the cells was carried out using standard protocols (FIG. 10).

The invention claimed is:

1. A polypeptide comprising an O-linked glycosylation sequence, wherein the O-linked glycosylation sequence comprises a sequence selected from SEQ ID Nos: 2-14, and wherein the O-linked glycosylation sequence is covalently bound to an O-glycan.

2. A composition comprising the polypeptide according to claim 1 and a pharmaceutically acceptable excipient.

3. An O-glycosylated recombinant protein conjugate comprising the polypeptide according to claim 1, wherein a molecule desirable to be attached to the recombinant protein is covalently linked to the O-glycan.

4. A composition comprising the O-glycosylated recombinant protein conjugate according to claim 3 and a pharmaceutically acceptable excipient.

* * * * *